United States Patent
Wang

(10) Patent No.: US 11,466,309 B2
(45) Date of Patent: Oct. 11, 2022

(54) MECHANICALLY-STRAINED OLIGONUCLEOTIDE CONSTRUCTS AND METHODS OF USING THE SAME

(71) Applicant: THE BOARD OF TRUSTEES OF THE UNIVERSITY OF ARKANSAS, Little Rock, AR (US)

(72) Inventor: Yong Wang, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 295 days.

(21) Appl. No.: 16/601,246

(22) Filed: Oct. 14, 2019

(65) Prior Publication Data

US 2020/0115738 A1   Apr. 16, 2020

Related U.S. Application Data

(60) Provisional application No. 62/744,828, filed on Oct. 12, 2018.

(51) Int. Cl.
   *C12Q 1/68*      (2018.01)
   *C12Q 1/6818*    (2018.01)
   *C12Q 1/6806*    (2018.01)

(52) U.S. Cl.
   CPC ......... *C12Q 1/6818* (2013.01); *C12Q 1/6806* (2013.01); *C12Q 2500/00* (2013.01); *C12Q 2523/303* (2013.01); *C12Q 2523/313* (2013.01); *C12Q 2563/107* (2013.01); *C12Q 2563/113* (2013.01); *C12Q 2563/116* (2013.01); *C12Q 2563/137* (2013.01)

(58) Field of Classification Search
   CPC ................ C12Q 1/6818; C12Q 1/6806; C12Q 2500/00; C12Q 2523/303; C12Q 2523/313; C12Q 2563/107; C12Q 2563/113; C12Q 2563/116; C12Q 2563/137
   See application file for complete search history.

(56) References Cited

U.S. PATENT DOCUMENTS 7,122,321 B2   10/2006   Pantoliano

FOREIGN PATENT DOCUMENTS

CN    107064258 A       8/2017
DE    102004034343 A1   2/2006

OTHER PUBLICATIONS

Yong Wang et al 2009 J. Phys.: Condens. Matter 21 335103 (Year: 2009).*
Wang et al. Biophysical Journal vol. 96 Mar. 2009 2344-2352 (Year: 2009).*
Mahtab et al. JACS, 1995, 117, 9099-9100 (Year: 1995).*
Bal, W., et al. "Genotoxicity of metal ions: chemical insights" Met Ions Life Sci 8 (2011): 319-373.
Baumann, C. G., et al. "Ionic effects on the elasticity of single DNA molecules." Proceedings of the National Academy of Sciences 94.12 (1997): 6185-6190.
Berger, T. J., et al. "Electrically generated silver ions: quantitative effects on bacterial and mammalian cells." Antimicrobial agents and chemotherapy 9.2 (1976): 357.
Beyer, M. K., et al. "Mechanochemistry: the mechanical activation of covalent bonds." Chemical Reviews 105.8 (2005): 2921-2948.
Brunet, A. et al., "Dependence of DNA persistence length on ionic strength of solutions with monovalent and divalent salts: a joint theory-experiment study ." Macromolecules 48.11 (2015): 3641-3652.
Choi B. et al, "Mimicking cAMP-dependent allosteric control of protein kinase A through mechanical tension." Journal of the American Chemical Society 128.26 (2006): 8541-8548.
Clever, G. H., et al. "DNA-metal base pairs." Angewandte Chemie International Edition 46.33 (2007): 6226-6236.
Cong, P., et al. "Revisiting the anomalous bending elasticity of sharply bent DNA." Biophysical journal 109.11 (2015): 2338-2351.
Draper, D. E. et al. "Ions and RNA folding." Annu. Rev. Biophys. Biomol. Struct. 34 (2005): 221-243.
Feng, Q. L., et al. "A mechanistic study of the antibacterial effect of silver ions on *Escherichia coli* and *Staphylococcus aureus*." Journal of biomedical materials research 52.4 (2000): 662-668.
Gogoi, S. K., et al. "Green fluorescent protein-expressing *Escherichia c oli* as a model system for investigating the antimicrobial activities of silver nanoparticles." Langmuir 22.22 (2006): 9322-9328.
Haque, M. A., et al. "An experiment-based model quantifying antimicrobial activity of silver nanoparticles on *Escherichia coli*." RSC advances 7.89 (2017): 56173-56182.
Hartwig, A.. "Role of magnesium in genomic stability." Mutation Research/Fundamental and Molecular Mechanisms of Mutagenesis 475.1-2 (2001): 113-121.
Hickenboth, Charles R., et al. "Biasing reaction pathways with mechanical force." Nature 446.7134 (2007): 423-427.
Ivanov, I. et al. "Unraveling the three-metal-ion catalytic mechanism of the DNA repair enzyme endonuclease IV." Proceedings of the National Academy of Sciences 104.5 (2007): 1465-1470.
Lipfert, J., et al. "Understanding nucleic acid-ion interactions." Annual review of biochemistry 83 (2014): 813-841.
Nies, D. H. et al. "Transition Metal Homeostasis" EcoSal Plus 2013; doi:10.1128/ecosalplus.5.4.4.3.
Ono, A., et al. "Specific interactions between silver (I) ions and cytosine-cytosine pairs in DNA duplexes." Chemical communications 39 (2008): 4825-4827.
Qu, H. et al. "The complete bending energy function for nicked DNA." EPL (Europhysics Letters) 94.1 (2011): 18003.
Qu, H., et al. "Critical torque for kink formation in double-stranded DNA." Physical Review X 1.2 (2011): 021008.
Qu, H., et al. "Rapid and label-free strategy to isolate aptamers for metal ions." ACS nano 10.8 (2016): 7558-7565.

(Continued)

*Primary Examiner* — Jezia Riley
(74) *Attorney, Agent, or Firm* — Quarles & Brady, LLP

(57) ABSTRACT

Disclosed herein are mechanically-strained oligonucleotide constructs comprising two oligonucleotides that when hybridized results in a bent double-stranded oligonucleotide. The constructs may be used to probe oligonucleotide interactions with an analyte to detect interactions with metal ions or compounds.

11 Claims, 20 Drawing Sheets

Specification includes a Sequence Listing.

(56) References Cited

OTHER PUBLICATIONS

Qu, H., et al. (2010). The elastic energy of sharply bent nicked DNA. EPL (Europhysics Letters) 90, 18003-18003.
Rotake, D., et al. (2018). Heavy Metal Ion Detection in Water using MEMS Based Sensor. Materials Today: Proceedings 5, 1530-1536.
Shamsi, M. H. et al. "Interactions of metal ions with DNA and some applications." Journal of Inorganic and Organometallic Polymers and Materials 23.1 (2013): 4-23.
Shukla, S. et al. "Probing differential Ag+-nucleobase interactions with isothermal titration calorimetry (ITC): Towards patterned DNA metallization." Nanoscale 1.1 (2009): 122-127.
Stellwagen, E. et al. "Quantitative analysis of monovalent counterion binding to random-sequence, double-stranded DNA using the replacement ion method." Biochemistry 46.7 (2007): 2050-2058.
Wang, M. D., et al. "Stretching DNA with optical tweezers." Biophysical journal 72.3 (1997): 1335.
Wu, Y., et al. A reagentless DNA-based electrochemical silver(I) sensor for real time detection of Ag(I)—the effect of probe sequence and orientation on sensor response. Biotechnology Journal 11, 788-796. 2016.
You, J., et al. (2017). A microcantilever-based silver ion sensor using DNA-functionalized gold nanoparticles as a mass amplifier. Nanotechnology 28, 245501.
Zhang, X.-B., et al. (2011). Metal Ion Sensors Based on DNAzymes and Related DNA Molecules. Annual Review of Analytical Chemistry 4, 105-128.
Zhou, L., et al. "Direct design of an energy landscape with bistable DNA origami mechanisms." Nano letters 15.3 (2015): 1815-1821.
Zhou, L., et al. "DNA origami compliant nanostructures with tunable mechanical properties." ACS nano 8.1 (2014): 27-34.
Zhou, Y., et al. "Antibacterial activities of gold and silver nanoparticles against *Escherichia coli* and bacillus Calmette-Guérin." Journal of nanobiotechnology 10.1 (2012): 19.

* cited by examiner

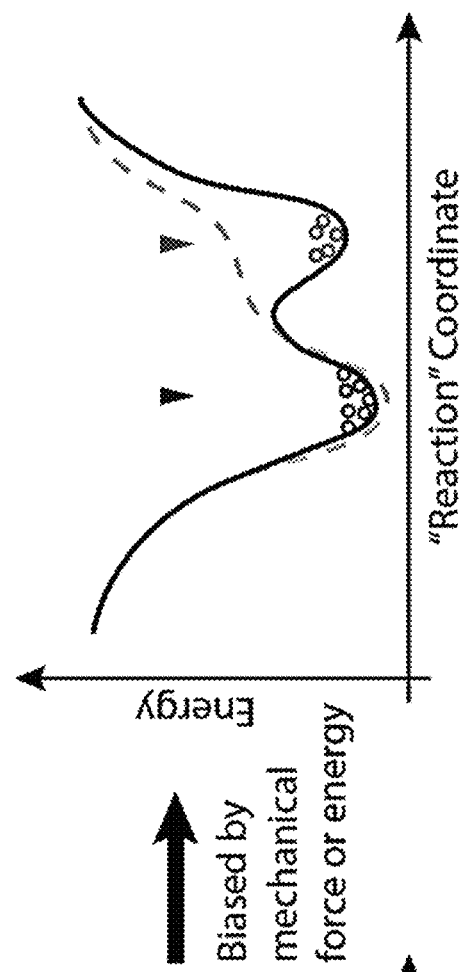
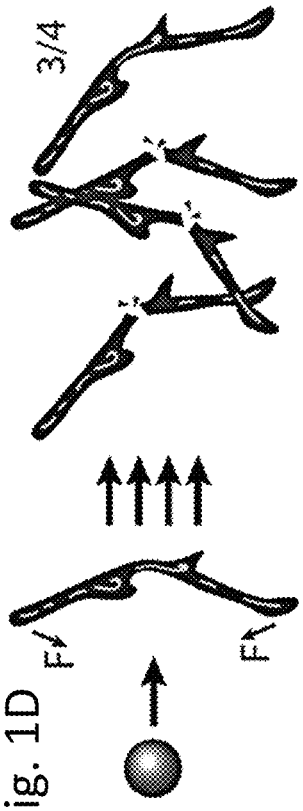
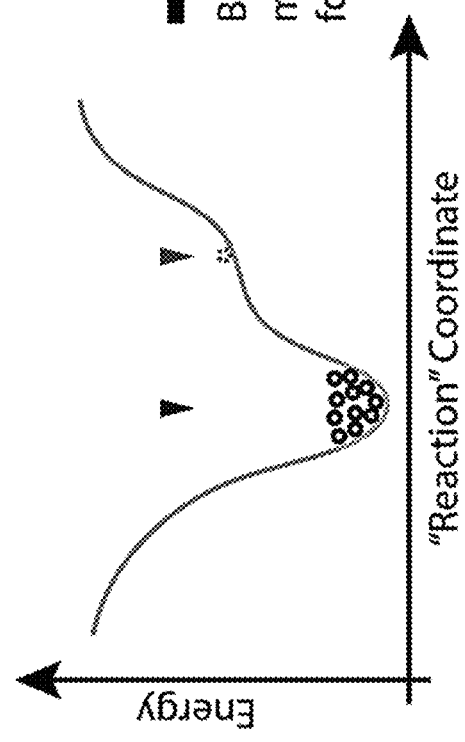
Fig. 1A
Fig. 1B
Fig. 1C
Fig. 1D

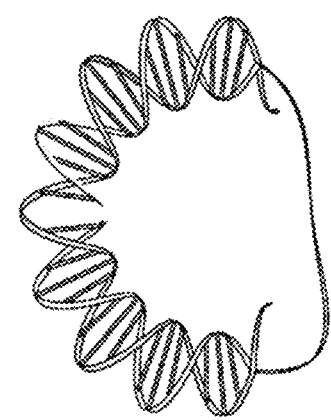
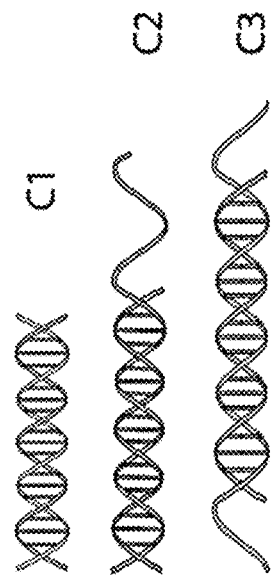
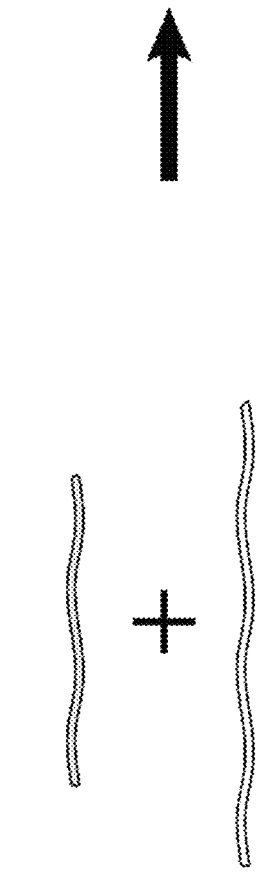
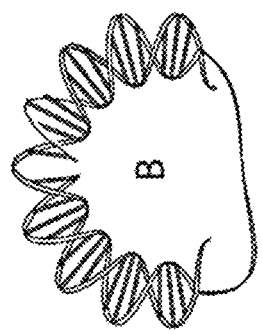
Fig. 1E
Fig. 1F
Fig. 1G

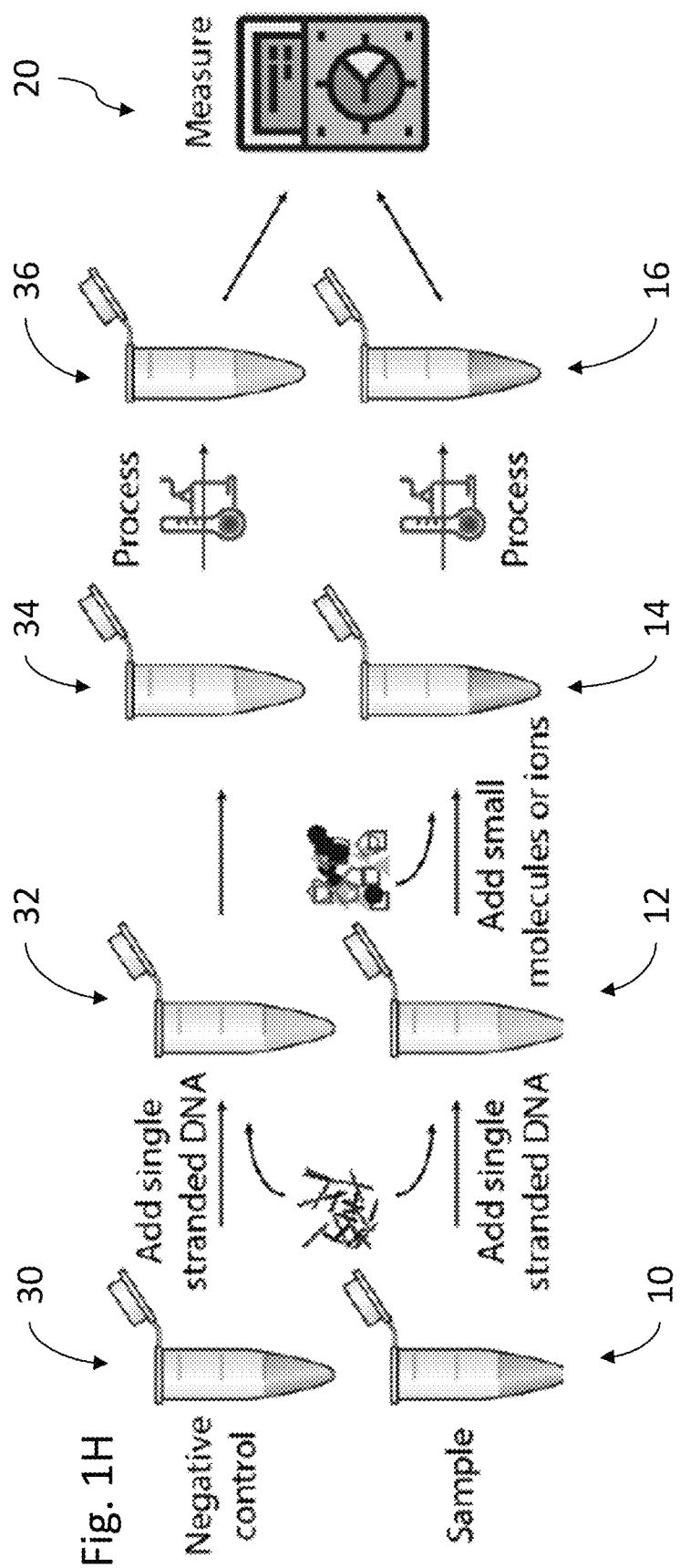

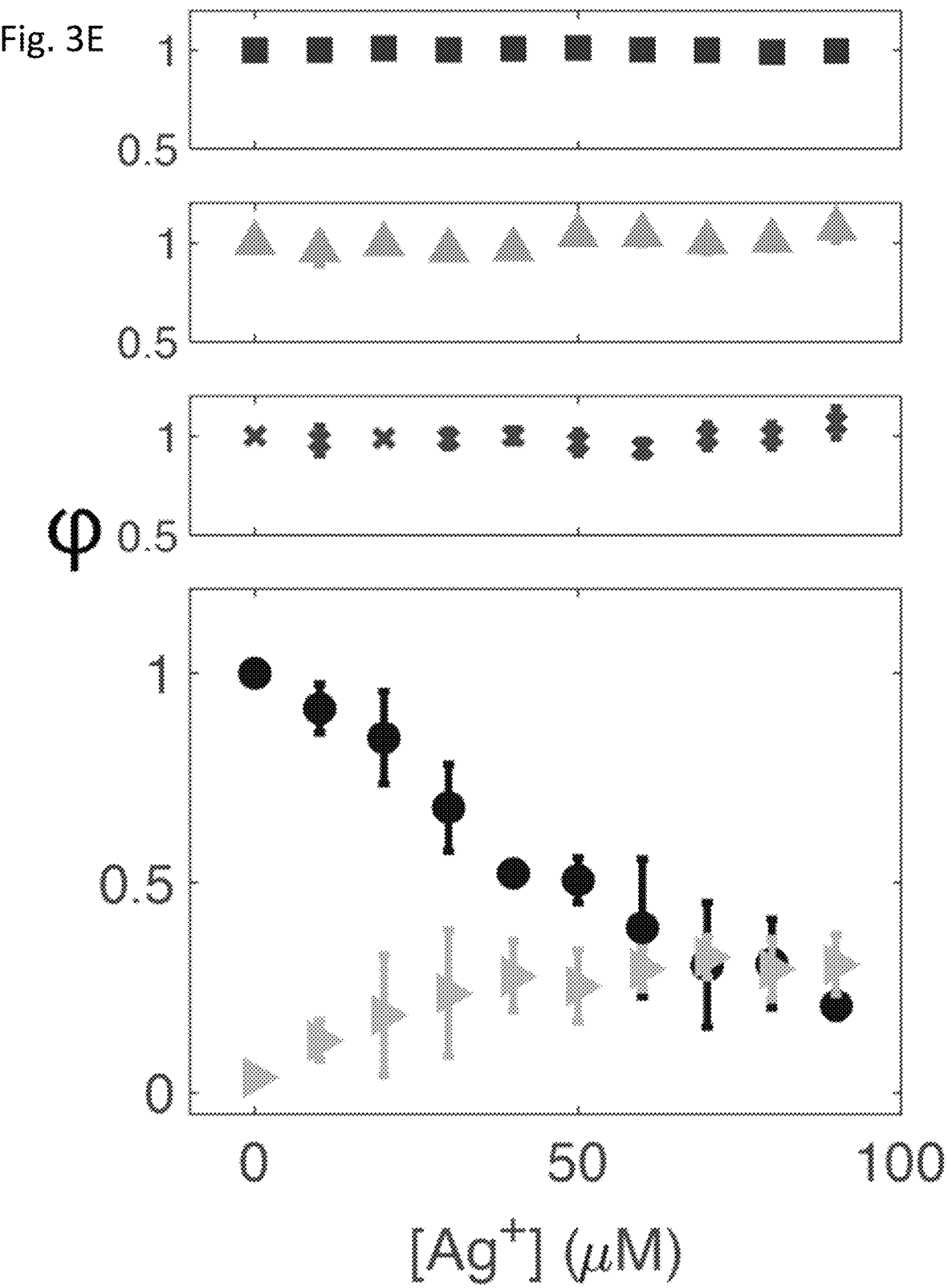

MECHANICALLY-STRAINED OLIGONUCLEOTIDE CONSTRUCTS AND METHODS OF USING THE SAME

BACKGROUND

Interactions of oligonucleotide and ions or other compounds, e.g., DNA-metal interactions, are essential for various fundamental processes in cells. For example, the formation of secondary and higher-order structures of nucleotides, DNA repair, and genomic stability require the presence, mediation, and/or participation of metal ions such as magnesium ions ($Mg^{2+}$). On the other hand, many metal ions can be toxic, resulting in DNA damage and cell death, which can accumulate and possibly lead to diseases such as cancers and other diseases. Studies have shown that $Ag^{2+}$, $Cu^{2+}$ and $Al^{3+}$ ions induce DNA damage and have genotoxicity. Therefore, it is important to understand the interactions between oligonucleotides and metal ions and other oligonucleotide interacting compounds.

These interactions, however, are not straightforward to measure directly. Most chemical and biochemical methods are not sensitive enough. The most well studied DNA-metal interactions using biochemical methods are DNA cleavages, but most DNA-metal interactions are much milder. Various spectroscopic methods have been used to study oligonucleotide interactions. These methods are often not sensitive enough (e.g., X-ray absorption spectroscopy) or require samples in the solid phase (e.g., electron paramagnetic resonance), rendering them not suitable for studies in solutions. Furthermore, sensitive techniques such as infrared spectroscopy, Raman spectroscopy and nuclear magnetic resonance spectroscopy typically require expensive equipment. Therefore, there is an urgent need for developing simple, sensitive, and cost-effective methods to study the interactions of oligonucleotides and various ions and compounds.

BRIEF SUMMARY OF THE INVENTION

Disclosed herein are mechanically-strained oligonucleotide constructs comprising two oligonucleotides that when hybridized results in a bent double-stranded oligonucleotide construct. The constructs may be used to probe oligonucleotide interactions with an analyte to detect interactions with metal ions or compounds.

The method for detecting the interaction of an analyte comprises providing a solution comprising the mechanically-strained oligonucleotide construct and detecting at least one detectable characteristic of the mechanically-strained oligonucleotide construct dependent on the analyte's concentration in the solution. The at least one detectable characteristic of the mechanically-strained oligonucleotide construct is the concentration of a first oligonucleotide or a second oligonucleotide. In some embodiments, the at least one detectable characteristic of the mechanically-strained oligonucleotide is a concentration of the mechanically-strained oligonucleotide construct, a component of the mechanically-strained oligonucleotide construct, a higher-order construct, or any combination thereof. In some embodiments, the at least one detectable characteristic of the mechanically-strained oligonucleotide is a spectroscopic feature.

The mechanically-strained oligonucleotide construct comprises a first oligonucleotide completely or partially hybridized to a second oligonucleotide. The first oligonucleotide comprises a first domain and a second domain in order from 5' to 3' and the second oligonucleotide comprises a first complementary domain, a single-stranded domain, and a second complementary domain in order from 5' to 3'. The first domain and the first complementary domain may be completely or partially complementary, capable of complete or partial hybridization with each other. The second domain and the second complementary domain may be completely or partially complementary, capable of complete or partial hybridization with each other. Upon hybridization of the first and second oligonucleotides, bent double-stranded oligonucleotide construct is formed. In some embodiments, the mechanically-strained oligonucleotide construct comprises a chromophore. In certain embodiments, the chromophore comprises donor fluorophore, an accepter fluorophore, or both the donor fluorophore and the accepter fluorophore. In particular embodiments, the construct comprises both the donor fluorophore and the accepter fluorophore. In certain embodiments, the construct comprises both the donor fluorophore and the accepter fluorophore linked to opposing ends of the first oligonucleotide.

In some embodiments, the solution comprising the mechanically-strained oligonucleotide construct further comprises an analyte. The analyte may be an ion, including a cation or an anion, or an oligonucleotide interacting compounds, including an oligonucleotide intercalating compound, an oligonucleotide groove binding compound, or a covalent oligonucleotide binding compound. Suitably the at least one detectable characteristic measurably changes depending on the amount of analyte present in the solution.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIGS. 1A-1H illustrate the strategy of the mechanical energy based amplifiers for probing interactions of DNA with metal ions. FIGS. 1A and 1B illustrate how perturbing a hypothetic energy landscape to redistribute molecules so that higher signals are detected. With the original, unperturbed energy landscape (FIG. 1A), fewer molecules are distributed on the detectable state (magenta arrow), producing lower signals. In contrast, after biasing the energy landscape by mechanical forces or energies (FIG. 1B), more "molecules" are redistributed on the detectable state (magenta arrow), "amplifying" the signals for detections. FIGS. 1C and 1D illustrate a simple analogy to illustrate the idea of mechanical energy based amplifiers using wooden sticks and marble balls. FIG. 1E illustrates self-assembly of a bent double-stranded DNA. FIG. 1F illustrates self-assembly of a bent double-stranded DNA with sequences CTG CTG AAT TCT GTG GAG TCG TCG TAT GTC (SEQ ID NO: 1) and CAC AGA ATT CAG CAG CAG GCA ATG ACA GTA GAC ATA CGA CGA CTC (SEQ ID NO: 2), as used in the Examples described below. FIG. 1G illustrates bent DNA molecules (construct B) as amplifiers vs. linear DNA molecules (constructs C1, C2, and C3 as described in Table 1) as negative controls. FIG. 1H presents a schematic illustration of the application for applying the self-assembled DNA for probing DNA interactions with small molecules or ions.

FIGS. 2A-2C show gel electrophoresis for linear DNA controls in the presence of $Mg^{2+}$ ions of 0-7 mM of construct C1 (FIG. 2A), construct C2 (FIG. 2B), and construct C3 (FIG. 2C). FIG. 2D shows gel electrophoresis for bent DNA in the presence of $Mg^{2+}$ ions of 0-7 mM. Lane SS: the long single-stranded DNA (45 bases) in the absence of $Mg^{2+}$ ions. FIG. 2E shows the dependence on $Mg^{2+}$ concentration of the intensities of the bands indicated by the corresponding markers in FIGS. 2A-2D, respectively from top to bottom. Error bars stand for the standard deviation of replicates. FIG. 2F shows interconversion between bent DNA monomers (circles in FIG. 2E) and relaxed dimers (▶ triangles in FIG. 2E). FIG. 2G shows the estimated change in the difference of free energy between the relaxed dimers and bent monomers as a function of $Mg^{2+}$ concentration. Estimations were carried out using either the bent monomer band only (B, squares) or both the bent monomer and relaxed dimer bands (B+R, circles).

FIGS. 3A-3G illustrate the probing DNA-$Ag^+$ interactions using bent DNA amplifiers. FIGS. 3A-3C show gel electrophoresis for linear DNA controls in the presence of $Ag^+$ ions of 0-90 µM of construct C1 (FIG. 3A), construct C2 (FIG. 3B), and construct C3 (FIG. 3C). FIG. 3D shows gel electrophoresis for bent DNA in the presence of $Ag^+$ ions of 0-90 µM. Lane SS: the long single-stranded DNA (45 bases) in the absence of $Ag^+$ ions. FIG. 3E shows the dependence on $Ag^+$ concentration of the intensities of the bands indicated by the corresponding markers in FIGS. 3A-3D, respectively from top to bottom. Error bars stand for the standard deviation of replicates. FIG. 3F shows interconversion between bent DNA monomers (circles in FIG. 3E) and unhybridized single strands (▶ triangles in FIG. 3E). FIG. 3G shows the estimated change in the difference of free energy between the unhybridized single-strands and bent monomers as a function of $Ag^+$ concentration. Estimations were carried out using either the bent monomer band only (B, squares) or both the bent monomer and unhybridized single-stranded bands (B+SS, circles).

FIGS. 4A-4G show gels of bent DNA amplifiers or linear DNA controls (C1, C2, and C3) in the presence of salts at increasing concentrations: (FIG. 4A) $MgCl_2$, (FIG. 4B) $MgSO_4$, (FIG. 4C) KCl, (FIG. 4D) $CaCl_2$, (FIG. 4E) $Al(NO_3)_3$, (FIG. 4F) $Zn(NO_3)_2$, and (FIG. 4G) $AgNO_3$.

FIGS. 5A-5G show intensities of the bands of bent DNA amplifiers (●) or linear DNA controls (C1: ◀, C3: △, C2: ▷) in the presence of various salts at increasing concentrations: (FIG. 5A) $MgCl_2$, (FIG. 5B) $MgSO_4$, (FIG. 5C) KCl, (FIG. 5D) $CaCl_2$, (FIG. 5E) $Al(NO_3)_3$, (FIG. 54F) $Zn(NO_3)_2$, and (FIG. 5G) $AgNO_3$. Black dashed lines are fittings using the modified Hill equation.

FIG. 6A shows fitted h and u values for the DNA interactions with inorganic salts. FIG. 6B compares u values for the salts.

FIGS. 7A-7G show gels of bent DNA amplifiers or linear DNA controls (C1, C2, and C3) in the presence of oligonucleotide interacting compounds at increasing concentrations: (FIG. 7A) guanidine, (FIG. 7B) putrescine, (FIG. 7C) spermidine, (FIG. 7D) ganciclovir, (FIG. 7E) ethidium bromide, (FIG. 7F) SYBR safe, and (FIG. 7G) thiamine.

FIGS. 8A-8G show intensities of the bands of bent DNA amplifies (●) or linear DNA controls (C1: ◀, C3: △, C2: ▷) in the presence small organic molecules at increasing concentrations: (FIG. 8A) guanidine, (FIG. 8B) putrescine, (FIG. 8C) spermidine, (FIG. 8D) ganciclovir, (FIG. 8E) ethidium bromide, (FIG. 8F) SYBR safe, and (FIG. 8G) thiamine. Black dashed lines are fittings using the modified Hill equation.

FIG. 9A shows fitted h and u values for the DNA interactions with the compounds. FIG. 9B compares u values for the organic molecules.

FIG. 10A shows the fluorescence spectra of bent DNA molecules in the presence of $Mg^{2+}$ ions at increasing concentrations, from 0 µM to 200 µM. The black arrow indicates the increase of $Mg^{2+}$ ions. FIG. 10B shows the dependence of the FRET efficiency on the concentration of $Mg^{2+}$ ions. The dashed line is the fitting of the data using the MM kinetics.

DETAILED DESCRIPTION OF THE INVENTION

Figure 2A:
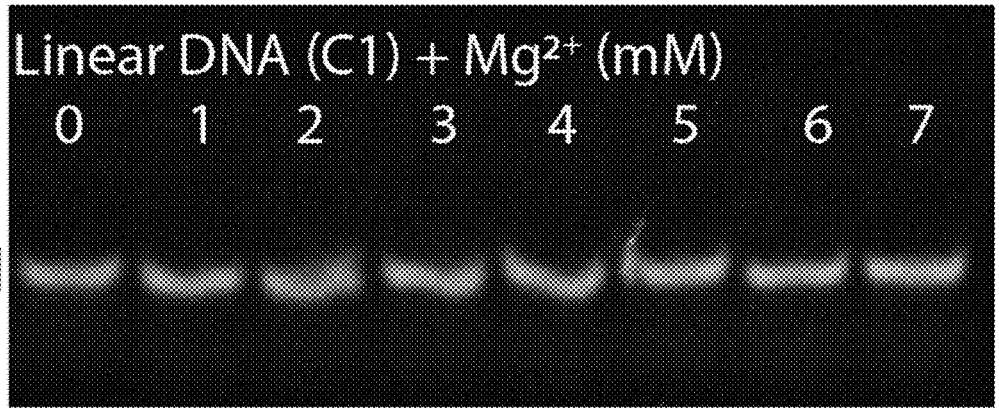
FIGS. 2A-2G illustrate the probing DNA-$Mg^{2+}$ interactions using bent DNA amplifiers.

We report the development of a sensitive, efficient, and cost-effective method to amplify and probe the interactions of oligonucleotides with ions or other compounds that may be readily performed on a laboratory setting. This method is based on perturbing energy landscapes using mechanical energy stored in bent oligonucleotide constructs. As shown in the Examples that follow, the mechanical energy based amplifiers were applied to examine the interactions between DNA and ions as well as DNA and oligonucleotide interacting compounds. We demonstrated that interaction between DNA and these analytes, which are not detectable using gel electrophoresis without amplification, can be easily measured using our molecular amplifiers. Moreover, we also show that the interaction of DNA with analytes may be spectroscopically detected. In addition, we showed quantitative details about the DNA interactions can be estimated using our method.

Many properties of a system (including the equilibrium and dynamics) are governed by the system's Hamiltonian H, or the potential energy V, which has been commonly referred to as the "energy landscape" of the system. We show that it is possible to perturb the potential energy of an oligonucleotide, modulating and/or biasing its chemical or biochemical system, to sensitively probe interactions with the oligonucleotide using methods commonly employed in laboratories.

Herein we report a new concept of exploiting mechanical energy to amplify the interactions between oligonucleotides and analytes, such as metal ions and oligonucleotide interacting compounds. We take advantage of mechanical energy stored in bent oligonucleotide constructs and developed a sensitive, cost-effective method to amplify and probe the interactions of oligonucleotides. The strategy of this method is illustrated in FIGS. 1A and 1B, where hypothetic energy landscapes along an oligonucleotide-analyte reaction coordinate are shown, assuming one of the local minima in the energy landscape (indicated by the magenta arrow) gives the detectable signal of the interaction. Without amplification (i.e., the normal linear oligonucleotide), the signal from the interaction at equilibrium may be too low to be detected. By perturbing the energy landscape using the bending energy stored in bent oligonucleotide molecules, more molecules may be distributed in the detectable state (magenta arrow), resulting in an amplification of the detectable signals. It is noted that the mechanical energy stored in the bent oligonucleotide does not necessarily introduce additional interactions. Instead, the mechanical energy improves the sensitivity for observing the interactions. A good analogy to illustrate this idea is shown in FIGS. 1C and 1D: marble balls are thrown onto wooden sticks. If the collisions are weak enough, the sticks rarely crack, producing "low signals" (FIG. 1C). In contrast, after applying stress and pre-bending the sticks so that they are close to breaking down, collisions at the same strength would result in higher number of cracked sticks, generating "higher signals" (FIG. 1D). The mechanical energy stored in the pre-bent sticks does not change their interactions with the balls; instead, it makes the signals much easier to be observed. In other words, the mechanical energy "amplifies" the signals.

The methods described herein use mechanically-strained oligonucleotide constructs. As used herein "mechanically-strained oligonucleotide constructs" (which may also be referred to as "mechanical energy based amplifiers" or, more simply, "amplifiers") comprise two oligonucleotides. As used herein, "oligonucleotides" mean DNA, RNA, or derivatives thereof, such as DNA or RNA derivatives having modified sugars, bases, or backbones or labels, dyes, quenchers, linkers, or terminal caps attached thereto. The first of the oligonucleotides comprising a first and second domain in order from 5' to 3'. The second of the oligonucleotides comprises a first complementary domain, a single-stranded domain, and a second complementary domain in order from 5' to 3'. The first domain and the first complementary domain are completely or partially complementary and capable of completely or partially hybridizing with each other and the second domain and the second complementary domain are completely or partially complementary and capable of completely or partially hybridizing with each other.

Exemplary embodiments of mechanically-strained oligonucleotide constructs are illustrated in FIGS. 1E and 1F. The first complementary domain of the long sequence hybridizes to the first domain of the short sequence, while the second complementary domain of the long sequence hybridizes to the second domain of the short sequence, leaving the middle single-stranded domain of the long sequence unhybridized. This design will produce, upon hybridization, a bent double-stranded oligonucleotide (containing a nick), while the single-stranded part is stretched. In some embodiments, the constructs have a constant torque less than a critical torque capable of causing the construct to kink. Suitably, the constant torque may be less than 27 pN nm. Constructs of this sort and their physical properties are described in H. Qu, C.-Y. Tseng, Y. Wang, A. J. Levine, and G. Zocchi, EPL (Europhysics Letters) 90, 18003 (2010); H. Qu and G. Zocchi, EPL (Europhysics Letters) 94, 18003 (2011); H. Qu, Y. Wang, C. Y. Tseng, and G. Zocchi, Physical Review X 1, 1 (2011); and P. Cong, L. Dai, H. Chen, J. R. C. Van Der Maarel, P. S. Doyle, and J. Yan, Biophysical Journal 109, 2338 (2015).

In other embodiments, the second oligonucleotide may comprise a circular oligonucleotide sequence.

The construct may be of any suitable size to probe the interaction of interest. In some embodiments, the first oligonucleotide comprises $N_1$ bases where $N_1$ is greater than or equal to 10 and/or less than or equal to 100. In particular embodiments, $N_1$ is greater than equal to 10, 15, 20, 25, 30, 35, 40, 45, or 50 and/or less than or equal to 100, 95, 90, 85, 80, 75, 70, 65, 60, 55, or 50, including any range therebetween. In some embodiments, the second oligonucleotide comprises $N_2$ bases where $N_2$ is greater than or equal to 15 and/or less than or equal to 180. In particular embodiments, $N_2$ is greater than equal to 15, 20, 25, 30, 35, 40, 45, 50, 55, 60, 65, 70, or 75 and/or less than or equal to 180, 175, 170, 165, 160, 155, 150, 145, 140, 135, 130, 125, 120, 115, 110, 105, or 100, including any range therebetween. Suitably, the mechanically-strained oligonucleotide construct comprises $N_d$ complementary base pairs where $N_d$ is greater than or equal to 10 and/or $N_d$ is less than or equal to 100. In particular embodiments, $N_d$ is greater than equal to 10, 15, 20, 25, 30, 35, 40, 45, or 50 and/or less than or equal to 100, 95, 90, 85, 80, 75, 70, 65, 60, 55, or 50, including any range therebetween. Suitably, the mechanically-strained oligonucleotide construct comprises $N_s$ unpaired bases where $N_s$ is greater than or equal to 5 and/or $N_s$ is less than or equal to 80. In particular embodiments, $N_s$ is greater than equal to 5, 10, 15, 20, 25, 30, 35, or 40 and/or less than or equal to 80, 75, 70, 65, 60, 55, 50, 45, or 40, including any range therebetween.

In certain embodiments, the sum of the number of bases in the first domain $N_{11}$ and the number of bases in the second domain $N_{12}$ of the first oligonucleotide equals $N_d$ and/or the sum of the number of bases in the first complementary domain $N_{21}$ and the number of bases in the second complementary domain $N_{22}$ of the second oligonucleotide equals $N_d$. In some embodiments, $N_{11}$ and $N_{21}$ comprise an equal number of bases and/or $N_{21}$ and $N_{22}$ comprise an equal number of bases $N_{11}$ and $N_{12}$ may be equal, but need not be. Exemplary embodiments include, without limitation, $N_{11}$ and $N_{12}$ equal $N_d/2$, $N_{11}$ equals $N_d/3$ and $N_{12}$ equals $2N_d/3$, $N_{11}$ equals $2N_d/3$ and $N_{12}$ equals $N_d/3$, $N_{11}$ equals $N_d/4$ and $N_{12}$ equals $3N_d/4$, $N_{11}$ equals $3N_d/4$ and $N_{12}$ equals $N_d/4$. $N_{21}$ and $N_{22}$ may be equal, but need not be. Exemplary embodiments include, without limitation, $N_{21}$ and $N_{22}$ equal $N_d/2$, $N_{21}$ equals $N_d/3$ and $N_{22}$ equals $2N_d/3$, or $N_{21}$ equals $2N_d/3$ and $N_{22}$ equals $N_d/3$, $N_{21}$ equals $N_d/4$ and $N_{22}$ equals $3N_d/4$, $N_{21}$ equals $3N_d/4$ and $N_{22}$ equals $N_d/4$.

The sequences of the first domain and the first complementary domain may be completely complementary or partially complementary. When the first domain and the first complementary domain are partially complementary, the domains may be at least 80% complementary, at least 85% complementary, at least 90% complementary, or at least 95% complementary. In some embodiments, melting temperature of the first domain and the first complementary domain is above room temperature. Suitably the melting temperature of the first domain and the first complementary domain is at least 30° C., at least 35° C., at least 40° C., at least 45° C., at least 50° C., at least 55° C., or at least 60° C.

The sequences of the second domain and the second complementary domain may be completely complementary or partially complementary. When the second domain and the second complementary domain are partially complementary, the domains may be at least 80% complementary, at least 85% complementary, at least 90% complementary, or at least 95% complementary. In some embodiments, melting temperature of the second domain and the second complementary domain is above room temperature. Suitably the melting temperature of the second domain and the second complementary domain is at least 30° C., at least 35° C., at least 40° C., at least 45° C., at least 50° C., at least 55° C., or at least 60° C.

The sequences of the first domain and the second domain may be completely complementary or partially complementary with the first complementary domain and the second complementary domain. When the first domain and the second domain are partially complementary with the first complementary domain and the second complementary domain, the domains may be at least 80% complementary, at least 85% complementary, at least 90% complementary, or at least 95% complementary. In some embodiments, melting temperature of the construct is above room temperature. Suitably the melting temperature of the construct is at least 30° C., at least 35° C., at least 40° C., at least 45° C., at least 50° C., at least 55° C., or at least 60° C.

In some embodiments, the mechanically-strained oligonucleotide construct comprises a chromophore. The mechanically-strained oligonucleotide construct may comprise two or more chromophores. The chromophores may be positioned on the mechanically-strained oligonucleotide construct to allow for detection of the at least one detectable characteristic. In some embodiments, the mechanically-strained oligonucleotide construct comprises two chromophores on the same oligonucleotide or different nucleotides. When the mechanically-strained oligonucleotide construct comprises two chromophores on the same oligonucleotide, the chromophores may be positioned on opposing ends of the same oligonucleotide.

A "chromophore" is a region in a molecule where the energy difference between two separate molecular orbital falls within the near-UV, visible, or near-IR spectrum. Electromagnetic radiation of the appropriate frequency irradiating the chromophore can thus excite an electron from the lower energy molecular orbital to the higher energy molecular orbit. Suitably the chromophore is a fluorophore. A "fluorophore" is a chromophore capable of re-emitting electromagnetic radiation when in an excited state. The re-emitted radiation has a lower frequency, i.e., lower energy or longer wavelength, than the radiation capable of exciting the fluorophore.

Chromophores should have at least one spectroscopic feature that depends on an analyte's concentration in solution. A "spectroscopic feature" is any observable characteristic indicative of the chromophores interaction with electromagnetic radiation. Exemplary spectroscopic features include, without limitation, absorption spectra, emission spectra, relaxation rates, energy transfer efficiencies, or coupling strengths.

The mechanically-strained oligonucleotide construct may comprise two chromophores. Suitably the two chromophores are a donor fluorophore and an acceptor fluorophore. Donor and acceptor fluorophores are suitably matched when emitted radiation of the donor fluorophore is capable of exciting an electron between molecular orbitals of the acceptor fluorophore. Suitably the donor and acceptor fluorophores are capable of fluorescence resonance energy transfer (FRET). "Fluorescence resonance energy transfer" or "FRET" is a mechanism describing energy transfer between two chromophores where a donor in its excited state transfers energy to the acceptor chromophore. The energy transfer is through nonradiative dipole-dipole couplings. As a result, the efficiency of this energy transfer is inversely proportional to the sixth power of the distance between the donor and acceptor, making it sensitive to small changes in distance.

The method comprises providing a solution comprising the mechanically-strained oligonucleotide construct. The solution may be a hybridization solution. As used herein, "hybridization solution" means a solution comprising components for preparing a mechanically-strained oligonucleotide construct such as the first and second oligonucleotide. The hybridization solution comprises a mechanically-strained oligonucleotide construct comprising a first oligonucleotide completely or partially hybridized to a second oligonucleotide, possibly in equilibrium with construct components, e.g., single-stranded first and second oligonucleotides, and/or higher-order oligonucleotide construct. As used herein, "higher-order oligonucleotide constructs" comprise more than one first oligonucleotide and/or more than one second oligonucleotide partially or completely hybridized with each other, e.g., dimers comprising two of each of the first and second oligonucleotides or trimers comprising three of each of the first and second oligonucleotides. The hybridization salutation may further comprise a buffer or other components suitable for promoting the partial or complete hybridization of the first oligonucleotide to the second oligonucleotide to form the construct. The hybridization solution may be an aqueous solution. Preferably the hybridization solution allows constructs to be present in equilibrium around room temperature, e.g., between about 15° C. to about 30° C.

The solution may further comprise an analyte. When the solution comprises the analyte, the solution may be termed an "interacting solution". As used herein, "analyte" means any molecular or chemical species capable of interacting with an oligonucleotide. In some embodiments, the analyte is an ionic species or a neutral species. Ionic species include cationic species such as metal ions or organic ions or anions. Metal ions include, without limitation, Group 1 metal ions, Group 2 metal ions, transition metal ions such as Group 6, 7, 8, 9, 10, 11, or 12 metal ions, or post-transition metal ions such as Group 13 or 14 metal ions. Exemplary metal ions include, without limitation, $Li^+$, $Na^+$, $K^+$, $Rb^+$, $Cs^+$, $Mg^{2+}$, $Ca^{2+}$, $Sr^{2+}$, $Ba^{2+}$, $Cr^{3+}$, $Mn^{2+}$, $Fe^{2+}$, $Fe^{3+}$, $Co^{2+}$, $Ni^{2+}$, $Cu^{2+}$, $Ag^+$, $Au^+$, $Au^{3+}$, $Zn^{2+}$, $Cd^{2+}$, $Hg^+$, $Pb^{2+}$, and $Al^{3+}$. Neutral species and organic ions may include an oligonucleotide interacting compound. As used herein, "oligonucleotide interacting compound" includes any compound or species capable of binding, associating, or otherwise interacting, at least temporarily or at low equilibrium concentrations, with an oligonucleotide. Exemplary oligonucleotide interacting compounds include, without limitation, oligonucleotide intercalating compounds, oligonucleotide groove binding compounds, or covalent oligonucleotide binding compounds. The analyte may be introduced into the solution prior to, with, or after mechanically-strained oligonucleotide construct has been introduced into the solution.

The method also comprises detecting at least one detectable characteristic of the mechanically-strained oligonucleotide. A "detectable characteristic" is any characteristic indicative of the presence or absences of an interaction of the mechanically-strained oligonucleotide with an analyte that can be detected. Suitably, the detectable characteristic is detected by any suitable methods, including, without limitation, electrophoresis or spectroscopy.

FIG. 1H illustrates an exemplary method for probing oligonucleotide interactions with an analyte. In a first step 10, a sample is provided. Oligonucleotides for preparing a mechanically-strained oligonucleotide construct may be introduced into the sample 12, thereby forming a hybridization solution. Analyte may be added to the hybridization solution 14, thereby forming an interaction solution. Optionally, the interaction solution is processed 16 to facilitate detection. Finally, the solution is measured 20 to detect the detectable characteristic.

Control samples may also be prepared and analyzed by the methods described above. The notable difference is that the step of contacting the construct and the analyte is to be avoided. The hybridization solution may be processed or separated to prepare a separated control solution for isolating the construct from other components in the hybridization solution. In a first step 30, a sample is provided. Oligonucleotides for preparing a mechanically-strained oligonucleotide construct may be introduced into the sample 32, thereby forming a hybridization solution. In step 34, the solution is processed as in step 14 but, notably, the analyte is not added. Optionally, the interaction solution is processed 36 to facilitate detection. Finally, the solution is measured 20 to detect the detectable characteristic. As a control sample, the processing and detection steps should be performed under substantially identical conditions as the sample.

In some embodiments, the solution comprising the mechanically-strained oligonucleotide construct and, optionally, the analyte may be processed by separating the solution to prepare a separated interaction solution for the purpose of isolating the construct from other components in the interaction solution. Methods for separating chemical components known in the art and include techniques such as electrophoresis (including gel or capillary electrophoresis), chromatography (including high-performance liquid chromatography (HPLC), thin-layer chromatography, countercurrent chromatography, size-exclusion chromatography, ion chromatography, or affinity chromatography), adsorption, magnetic separation, as well as other separation methods. The separated solution may additionally comprise isolated single-stranded oligonucleotides or high-order oligonucleotide constructs.

The concentration of the mechanically-strained oligonucleotide constructs in the separated solution may then be measured or detected. Methods of detecting components in separated solution are known in the art and include techniques such as staining, imaging, radiodetection, fluorescent detection, as well as other detection methods. The concentrations of other isolated components such as single-stranded oligonucleotides or high-order oligonucleotide constructs may also be measured or detected.

The method may further comprise comparing the concentration of one or more components of the separated interaction solution and/or the separated control solution. In some embodiments, the method comprises comparing the concentration of the mechanically-strained oligonucleotide construct of the separated interaction solution and the concentration of the mechanically-strained oligonucleotide construct of the separated control solution. In certain embodiments, the method comprises comparing one or more addition separated components, including comparison of the concentration of the single-stranded first oligonucleotide, the concentration of the single-stranded second oligonucleotide, and/or the concentration of the higher order oligonucleotide construct of the separated interaction solution and the concentration of the single-stranded first oligonucleotide, the concentration of the single-stranded second oligonucleotide, and/or the concentration of the higher order oligonucleotide construct of the separated control solution. As shown in the Examples that follow, comparison of the concentrations of the constructs in the separated interaction and control solutions can provide qualitative and quantitative information on the change in free energy between the presence and absence of the analyte. In other cases, comparison of the concentrations of the constructs in the separated interaction and control solutions can only provide qualitative information on the change in free energy between the presence and absence of the analyte. A comparison of additional components may be needed to provide quantitative information as well as qualitative information on the change in free energy between the presence and absence of the analyte.

The Examples below show that these mechanical energy based amplifiers may be applied to examine the interactions between DNA and analytes. We demonstrated that interactions between DNA and analytes, which are not detectable using gel electrophoresis without amplification, can be easily measured using our molecular amplifiers. In addition, we showed that our method is capable of obtaining quantitative details about the DNA-analyte interactions.

In some embodiments, the solution comprising the mechanically-strained oligonucleotide construct and, optionally, the analyte may be processed by irradiating the solution. The spectroscopic feature of the mechanically-strained oligonucleotide constructs in the irradiated solution may then be measured or detected. Methods for irradiating solutions or samples and methods for detecting spectroscopic features are known in the art. Suitably, these methods include various spectroscopies. Exemplary spectroscopies include, without limitation, fluorescence spectroscopy, FRET spectroscopy, absorption or transmission spectroscopy, IR spectroscopy, or Raman spectroscopy. In particular embodiments, the solution is irradiation with electromagnetic radiation capable of exciting an electron from one molecular orbital to another higher energy molecular orbital.

The method may further comprise comparing the spectroscopic feature of one or more components of the separated interaction solution and/or a control solution. In some embodiments, the method comprises comparing the spectroscopic feature of the mechanically-strained oligonucleotide construct of the irradiated solution and the spectroscopic feature of the mechanically-strained oligonucleotide construct of the irradiated control solution. As shown in the Examples that follow, comparison of the spectroscopic features of the constructs in the irradiated and control solutions can provide qualitative and quantitative information.

The Examples below show that these mechanical energy based amplifiers may be applied to examine the interactions between DNA and analytes. We demonstrated that FRET efficiency is sensitive to the concentration of the analyte . . . .

To conclude, we developed a simple and cost-effective method to amplify and probe the interactions between oligonucleotides and analytes by taking advantage of mechanical energy stored in bent oligonucleotide constructs. We demonstrated the efficacy of these mechanical energy based amplifiers by applying them to examine the interactions between DNA and various analytes. By perturbing the energy landscape, our method amplifies the DNA interactions, making it sensitive and capable of detecting interactions with DNA that are not detectable using the same biochemical assay. Our method is sensitive and cost-effective, without requiring sophisticated and/or expensive equipment. The method is therefore useful broadly for various applications involving interactions of oligonucleotides with ions, molecules, reagents, and drugs Miscellaneous Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

1. K. G. Barki, et al. Annals of Surgery Publish Ahead of Print (2018)
2. M. K. Beyer and H. Clausen-Schaumann, Chemical Reviews 105, 2921 (2005).
3. C. R. Hickenboth, et al. Nature 446, 423 (2007).
4. B. Choi, et al. Physical Review Letters 95, 078102 (2005).
5. B. Choi and G. Zocchi, Journal of the American Chemical Society 128, 8541 (2006).
6. Y. Wang, A. Wang, H. Qu, and G. Zocchi, Journal of physics. Condensed matter: an Institute of Physics journal 21, 335103 (2009).
7. Sigel, H. Sigel, and R. K. O. Sigel, eds., Interplay between Metal Ions and Nucleic Acids, Metal Ions in Life Sciences (Springer Netherlands, 2012).
8. D. E. Draper, D. Grilley, and A. M. Soto, Annual Review of Biophysics and Biomolecular Structure 34, 221 (2005).
9. Ivanov, J. A. Tainer, and J. A. McCammon, Proceedings of the National Academy of Sciences 104, 1465 (2007).
10. Hartwig, Mutation Research/Fundamental and Molecular Mechanisms of Mutagenesis Micronutrients and Genomic Stability, 475, 113 (2001).
11. P. B. Tchounwou, et al. in Molecular, Clinical and Environmental Toxicology, Experientia Supplementum (Springer, Basel, 2012) pp. 133{164.
12. W. Bal, A. M. Protas, and K. S. Kasprzak, Metal Ions in Life Sciences 8, 319 (2011).
13. H. Qu, C.-Y. Tseng, Y. Wang, A. J. Levine, and G. Zocchi, EPL (Europhysics Letters) 90, 18003 (2010).
14. H. Qu and G. Zocchi, EPL (Europhysics Letters) 94, 18003 (2011).
15. H. Qu, Y. Wang, C. Y. Tseng, and G. Zocchi, Physical Review X 1, 1 (2011).
16. P. Cong, et al. Biophysical Journal 109, 2338 (2015).
17. M. D. Abramoff, et al. Biophotonics International 11, 36 (2005).
18. Schindelin, et al. Nature Methods 9, 676 (2012).
19. C. G. Baumann, et al. Proceedings of the National Academy of Sciences 94, 6185 (1997).
20. M. D. Wang, et al. Biophysical Journal 72, 1335 (1997).
21. Brunet, et al. Macromolecules 48, 3641 (2015).
22. D. Murugesapillai, et al. Nanoscale 9, 11327 (2017).
23. R. Phillips, J. Kondev, and J. Theriot, Physical Biology of the Cell (Garland Science, 2013).
24. T. J. Berger, et al. Antimicrobial Agents and Chemotherapy 9, 357 (1976).
25. M. A. Hague et al. RSC Advances 7, 56173 (2017).
26. Y. Zhou, et al. Journal of nanobiotechnology 10, 19 (2012).
27. Q. L. Feng, et al. Journal of Biomedical Materials Research 52, 662 (2000).
28. S. K. Gogoi, et al. Langmuir 22, 9322 559 (2006).
29. Ono, et al. Chemical Communications 0, 4825 (2008).
30. S. Shukla and M. Sastry, Nanoscale 1, 122 (2009).
31. G. H. Clever, C. Kaul, and T. Carell, Angewandte Chemie International Edition 46, 6226 (2007).
32. H. Qu, A. T. Csordas, J. Wang, S. S. Oh, M. S. Eisenstein, and H. T. Soh, ACS Nano 10, 7558 (2016).

EXAMPLES

Example 1: Electrophoretic Detection of DNA-Analyte Interaction

Materials and Methods

Synthesized single-stranded DNA molecules were purchased from Integrated DNA Technologies (IL, USA), and re-suspended in distilled water to a final concentration of 100 μM. The sequences of DNA strands for constructing bent DNA molecules and the controls (FIG. 1G) are listed in Table 1. The long strand of the bent molecule (construct B in FIG. 1G) has 45 bases, while the length of the short strand is 30. Upon hybridization, a circular construct is formed, with a double-stranded portion of 30 base pairs (with a nick) and a single-stranded portion of 15 bases (FIG. 1F). Three linear constructs (C1, C2, and C3 in FIG. 1G) were used as negative controls. Upon hybridization, C1 is double-stranded completely, while C2 and C3 have overhangs of single strands at one or two sides, respectively. The long strands for C2 and C3 are the same as the long one in the bent molecule.

TABLE 1

DNA sequences used in this study.
The labels of the constructs refer to their
schematic sketches shown in FIG. 1G.

| Construct | Sequence (5'-3') |
| --- | --- |
| B | CTG CTG AAT TCT GTG GAG TCG TCG TAT GTC (SEQ ID NO: 1) CAC AGA ATT CAG CAG CAG GCA ATG ACA GTA GAC ATA CGA CGA CTC (SEQ ID NO: 2) |
| C1 | GAG ATG TCA AGA ATT CCG TCA GCA C (SEQ ID NO: 3) GTG CTG ACG GAA TTC TTG ACA TCT C (SEQ ID NO: 4) |
| C2 | TAC TGT CAT TGC CTG CTG CTG AAT TCT GTG (SEQ ID NO: 5) CAC AGA ATT CAG CAG CAG GCA ATG ACA GTA GAC ATA CGA CGA CTC (SEQ ID NO: 2) |
| C3 | GTA TGT CTA CTG TCA TTG CCT GCT GCT GAA (SEQ ID NO: 6) CAC AGA ATT CAG CAG CAG GCA ATG ACA GTA GAC ATA CGA CGA CTC (SEQ ID NO: 2) |

Single strands were mixed at equal molar amount in hybridization buffer (0.4 mM Tris, 0.5 mM NaCl) to reach a final concentration of 2 µM with $Mg^{2+}$ or $Ag^+$ ions at various concentrations ($[Mg^{2+}]$=0, 1, 2, 3, 4, 5, 6, 7 mM; $[Ag^+]$=0, 10, 20, . . . , 80, 90 µM). $Mg^{2+}$ and $Ag^+$ ions were provided from aqueous solutions of $MgCl_2$ and $AgNO_3$, respectively. The mixtures were heated to 75° C. for 2 minutes, and gradually cooled down to 22° C. (room temperature) in 5 hours. The mixtures were incubated at 22° C. for overnight to allow full equilibrium, followed by gel electrophoresis on the second day.

Polyacrylamide gels (12%) were prepared in the laboratory. Briefly, 3 mL of acrylamide/bis solutions (40%, Bio-Rad Laboratories, CA, USA), 1 mL of 10× tris-borate-EDTA (TBE) buffer (Bio-Rad Laboratories), 20 µL of freshly made ammonium persulfate (APS, 10\% in water, Thermo Fisher Scientific, MA, USA) and 6 mL of distilled water were mixed thoroughly and degassed for 10 minutes in vacuum. The mixture was poured into gel cast cassette immediately after adding 8 µL of tetramethylethylenediamine (TEMED) (Thermo Fisher Scientific), followed by incubation at room temperature for one to two hours to allow full gelation before use.

Five µL of the prepared DNA samples were mixed thoroughly with 5 µL of water and 2 µL of 6×DNA loading buffer (Bio-Rad Laboratories). The mixtures were loaded into the wells of the prepared gel. The gel electrophoresis (apparatus purchased from Edvotek Inc., DC, USA) was run at 100V for 45-60 minutes in 1×TBE buffer, followed by staining the gel with 1×SYBR Safe solution (Thermo Fisher Scientific) for 15-30 minutes with gentle shaking. The stained gel was then imaged with a typical exposure time of 2-5 seconds using a gel documentation system (UVP LLC., CA, USA). The acquired gel images were analyzed using ImageJ.

DNA-$Mg^{2+}$ Interactions

Figure 2B:
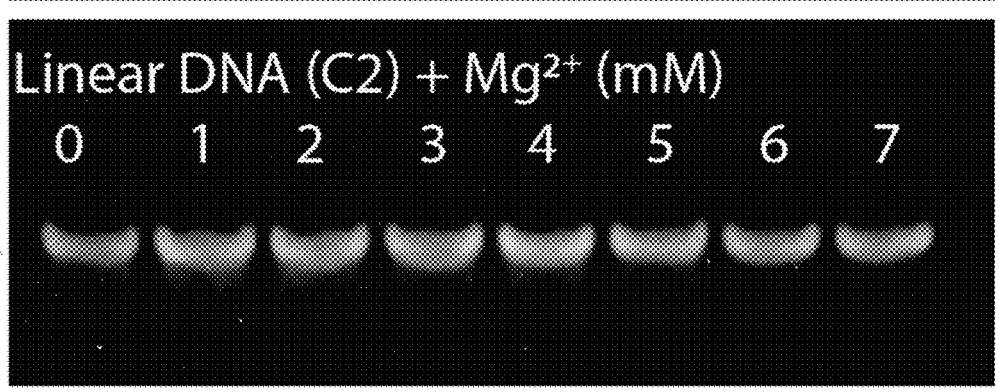
Figure 2C:
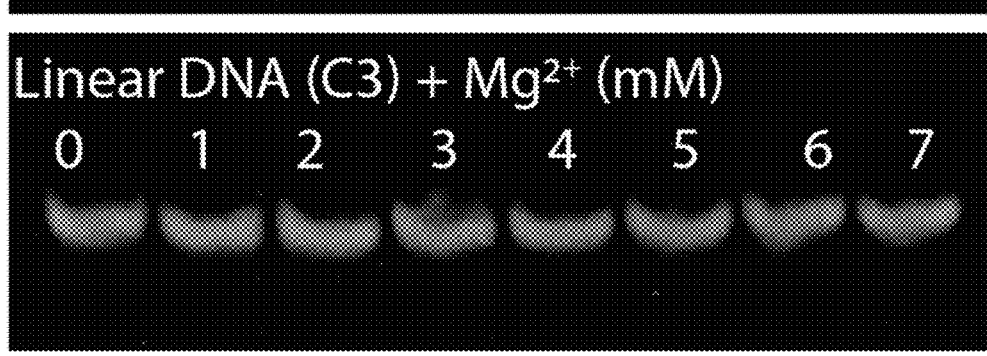
Figure 2D:
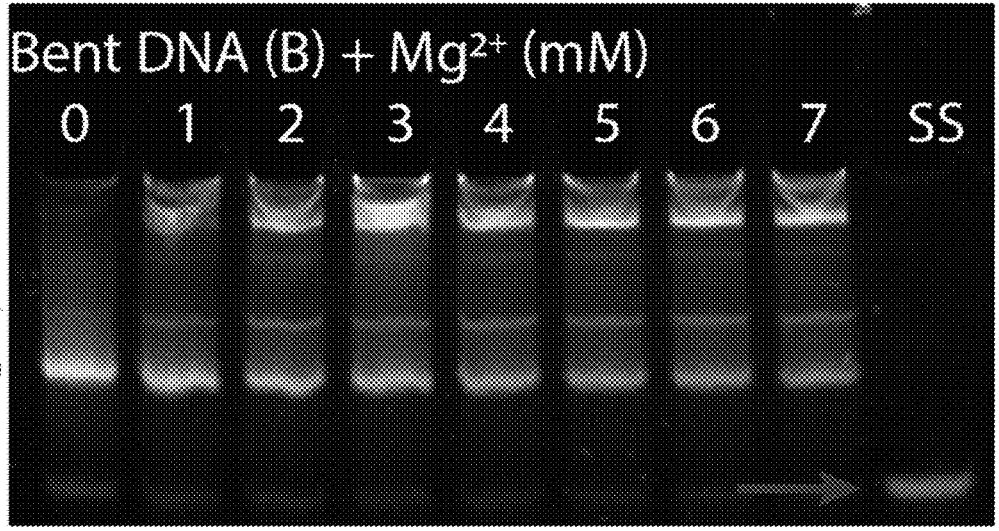
Figure 2E:
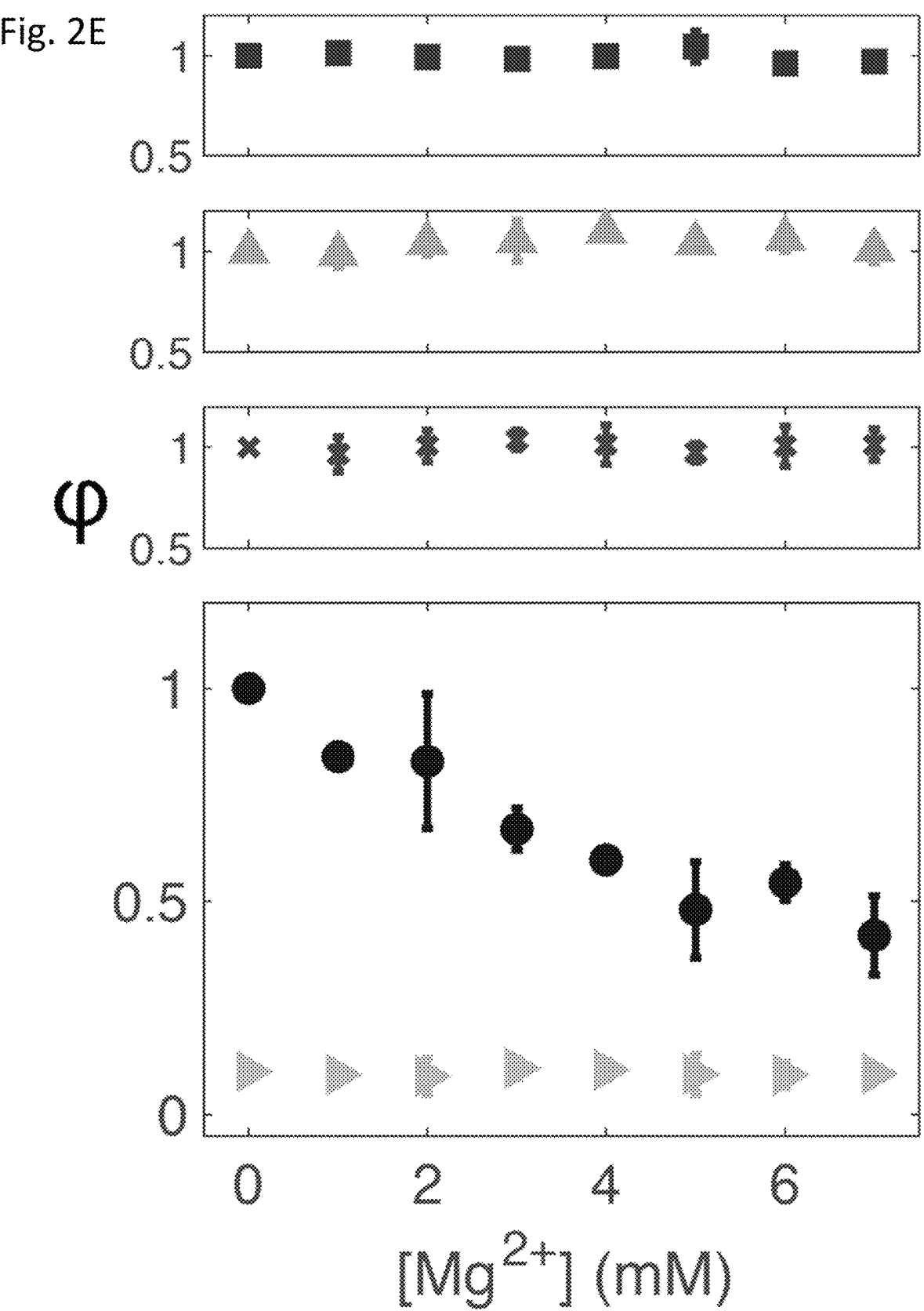

We first examined the well-known interaction between DNA and $Mg^{2+}$ ions using our method (FIGS. 2A-2G). As DNA molecules are negatively charged, electrostatic interactions are expected between $Mg^{2+}$ ions and DNA. In addition, electrostatic screening effects due to $Mg^{2+}$ ions stabilize double-stranded DNA molecules, which has been measured by magnetic tweezers, optical tweezers, and atomic force microscopy. However, such interactions between DNA and $Mg^{2+}$ ions cannot be easily observed with standard chemical/biochemical assays such as gel electrophoresis. For example, short linear double-stranded DNA molecules treated with $Mg^{2+}$ from 0 mM (control) to 7 mM did not show any difference in gel electrophoresis (FIG. 2A, indicated by squares). To quantify this observation, we measured the band intensities using ImageJ and compared them with the control (i.e., $[Mg^{2+}]$=0 mM), and observed a flat curve (squares in FIG. 2E). In contrast, when amplifying the signal of DNA-$Mg^{2+}$ interactions using the bent DNA molecules, the effect of $Mg^{2+}$ at the same concentrations (0-7 mM) is quite obvious (FIG. 2D): the intensity of the bent DNA band (indicated by circles in FIG. 2D) decreased as the concentration of $Mg^{2+}$ increased. In addition, we found that the dependence on $Mg^{2+}$ concentration of the intensity of the bent DNA band is roughly linear (circles in FIG. 2E). We note that a change was observed for $[Mg^{2+}]$=1 mM with the bent DNA amplifiers, while such a change was absent with $[Mg^{2+}]$=7 mM without amplification, indicating that the "amplification gain" of our bent DNA amplifiers for probing DNA-$Mg^{2+}$ interactions is at least 7. To exclude the possibility that the observed change in the gel electrophoretic pattern is due to the single-stranded portion of the bent molecules, we performed control experiments with linear DNA molecules that contain both double-stranded and single-stranded parts (constructs C2 and C3). We observed little changes for constructs C2 and C3 in the presence of 1-7 mM $Mg^{2+}$ as shown in FIGS. 2C and 2E (▲ triangles and ×, respectively). This observation suggests that the bent double-stranded DNA and the stored elastic energy are critical to detecting the DNA-$Mg^{2+}$ interactions.

In addition, our mechanical energy based amplifiers are capable of reporting quantitatively the interaction between $Mg^{2+}$ and DNA molecules. FIG. 2B shows that bands with heavier molecular weights appeared in the presence of $Mg^{2+}$ ions (above and at the green triangle in FIG. 2D). Previous studies by Qu et al. showed that these bands correspond to higher-order oligomers: for example, two monomers form a dimer; one monomer and one dimer (or three monomers) form a trimer; one monomer and one trimer (or four monomers) form a tetramer. The intensities of the bands with heavier molecular weight increased as the concentration of $Mg^{2+}$ increased, while the intensities of the bent monomer bands (blue circle) decreased. This observation suggests that $Mg^{2+}$ ions favored the interconversion from the bent DNA monomers to the relaxed DNA dimers and oligomers (FIG. 2F). A complete quantitative understanding of the observation requires taking into account all the possible reactions; however, for simplicity, here we focus only on the interconversion ("reaction") between monomers and dimers (FIG. 2F).

The interconversion between the monomers and dimers can be understood by starting with the chemical potential of solute molecules $\mu_s$ in water, $$\mu_s = \epsilon_s + k_B T \ln\left(\frac{N_s}{N_w}\right) = \epsilon_s + k_B T \ln(x_s) \quad (1)$$

where $\epsilon_s$ is the energy of each solute molecule, $k_B$ the Boltzmann constant, T the temperature, $N_s$ the number of solute molecules, $N_w$ the number of water molecules, and $x_s = N_s/(N_w+N_s) \approx N_s/N_w$ the molar fraction of the solute molecules. At equilibrium, we have $\mu_r = 2\mu_b$, where $\mu_r$ is the chemical potential of a relaxed DNA dimer and $\mu_b$ the chemical potential of a bent DNA monomer. Therefore, we have, $$\epsilon_r - 2\epsilon_b = k_B T \ln\left(\frac{x_b^2}{x_r}\right) \quad (2)$$

The difference in the free energy between half a dimer and a single bent DNA molecule is then $$\Delta\epsilon = \frac{\epsilon_r}{2} - \epsilon_b = k_B T \ln(x_b) - \frac{1}{2} k_B T \ln(x_r) \quad (3)$$

As a result, this difference $\Delta\epsilon$ can be estimated from the molar fractions of the bent DNA monomers and the relaxed dimers, which are proportional to the band intensities, $x_b = \beta I_b$ and $x_r = \beta I_r/2$, where $\beta$ is a constant. Note that, as the length of the relaxed dimers are twice that of the monomers, each dimer contributes twice the intensity of a monomer. Since the intensity of the dimer bands remains almost constant (▶ triangles in FIGS. 2D and 2E), the observed decrease in the band intensity of the bent DNA monomers (blue circles in FIG. 2E) in the presence of [Mg β $I_b$] suggests that $\Delta\epsilon$ decreased as [Mg$^{2+}$] increased.

More quantitatively, we estimated the effect of Mg$^{2+}$ ions on DNA (i.e., the change of $\Delta\epsilon$ in the presence (+) and absence (−) of Mg$^{2+}$ ions) by $$\Delta\Delta\epsilon = \Delta\epsilon^+ - \Delta\epsilon^- = k_B T \left[\ln\left(\frac{x_b^+}{x_b^-}\right) - \frac{1}{2}\ln\left(\frac{x_r^+}{x_r^-}\right)\right] \quad (4)$$

If we normalize the molar fractions to the control (i.e., [Mg$^{2+}$]=0 mM), $\varphi_b^- = x_b^-/x_b^- = 1$, $\varphi_b^+ = x_b^+/x_b^-$, $\varphi_r^- = x_r^-/x_r^-$, and $\varphi_r^+ = x_r^+/x_r^-$, we have $$\Delta\Delta\epsilon = k_B T \left[\ln(\varphi_b^+) - \frac{1}{2}\ln\left(\frac{\varphi_r^+}{\varphi_r^-}\right)\right] \quad (5)$$

Figure 2G:
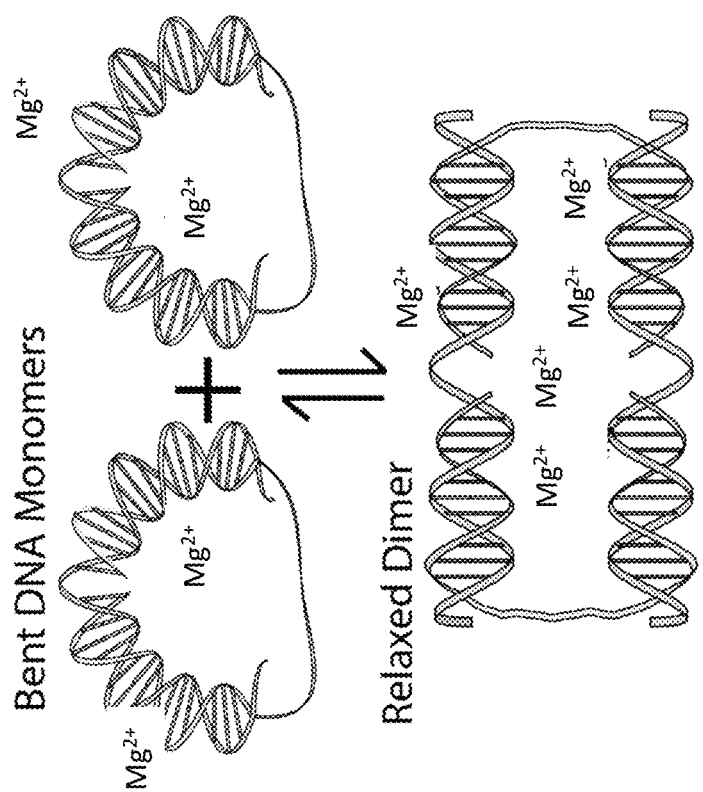
Figure 2F:
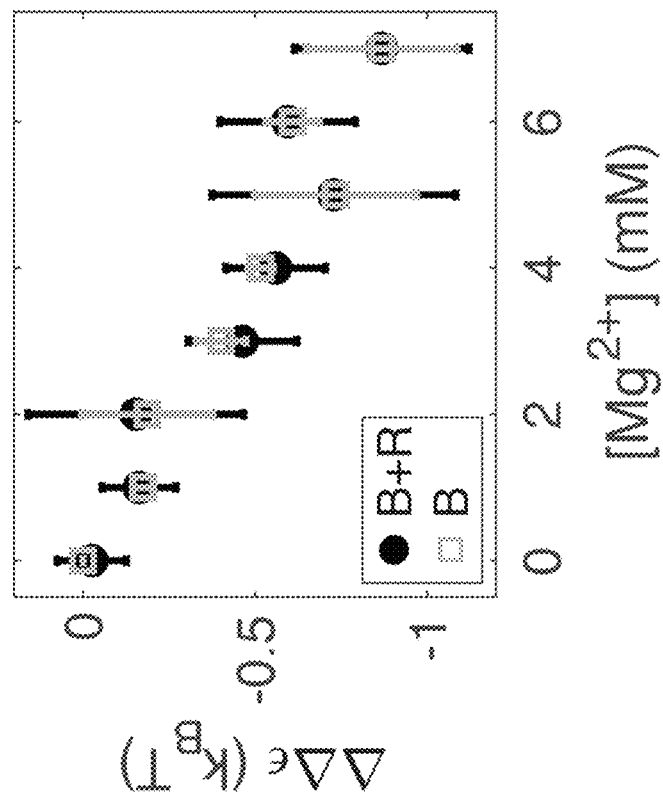

Using the data in FIG. 2E (both blue circles and green triangles), it was found that $\Delta\Delta\epsilon$ decreases linearly as the concentration of Mg$^{2+}$ increases, as shown in FIG. 2G (circles).

Note that the free energy in each bent DNA monomer consists various parts: the bending elastic energy ($\epsilon_e$), the hybridization energy ($\epsilon_h$), the electrostatic interactions between the negatively charged DNA (both double-stranded and single-stranded) and positively charged Mg$^{2+}$ ions ($\epsilon_{esi}$), the electrostatic energy inside the DNA molecules ($\epsilon_{esn}$), the entropic elastic energy of the single-stranded segments ($\epsilon_{ss}$), and the interactions between the nicks and Mg$^{2+}$ ions ($\epsilon_{ni}$), $$\epsilon_b = \epsilon_e + \epsilon_h + \epsilon_{esi} + \epsilon_{esn} + \epsilon_{ss} + \epsilon_{ni} + \quad (6)$$

It is likely that Mg$^{2+}$ ions play a role in all these terms, and $\Delta\Delta\epsilon$ reports the change of the total interaction between Mg$^{2+}$ ions and DNA (or the total effect of Mg$^{2+}$ ions on DNA molecules). In addition, previous experiment and simulations suggested that nicks promote DNA base-pair disruption and reduce DNA bending energy for sharply bent DNA. The energy release due to the nicks could result in two conformations of circular DNA (sharp kink vs. smooth bending), which likely co-exist. Therefore, it is practically difficult to de-convolve and separate the c terms. Nonetheless, no matter what the exact mechanisms are for the "reactions", it is clear that bending the DNA molecules is crucial and required for perturbing the energy landscape and amplifying the DNA-Mg$^{2+}$ interactions.

Furthermore, we examined the possibility of using the dependence of $\Delta\Delta\epsilon$ on the molar fraction of the bent DNA monomer $\varphi_b$ to capture the main feature of $\Delta\Delta\epsilon$ in the presence of Mg$^{2+}$ ions (i.e., $\Delta\Delta\epsilon$ decreases as [Mg$^{2+}$] increases). For this purpose, we estimated $\Delta\Delta\epsilon$ by considering the first term and ignoring the other bands, $$\Delta\Delta\epsilon \sim k_B T \ln(\varphi_b^+) \quad (7)$$

It turns out that the estimations from the bent monomer only (squares in FIG. 2G) are very close to the calculations using both the bent monomer and the relaxed dimer (circles in FIG. 2G).

DNA-Ag$^+$ Interactions

With the successful application of our bent DNA amplifiers to study DNA-Mg$^{2+}$ interactions, we exploited them to investigate the interactions of DNA with Ag$^+$ ions. The significance of DNA-Ag$^+$ interactions includes their genotoxicity and potential uses as antibiotic alternatives. For example, it has been reported that Ag$^+$ ions at <100 µM concentrations show significant antibiotic activities against bacteria. More importantly, it has been argued that it is more difficult for bacteria to develop resistance to Ag$^+$ ions compared to commonly prescribed antibiotics. Therefore, it is of great interest to understand the antibiotic mechanism of Ag$^+$ ions, which includes DNA-Ag$^+$ interactions. It was measured that Ag$^+$ ions caused DNA condensation in bacteria; however, this result could not be verified previously by in vitro experiments such as gel electrophoresis.

Figure 3A:
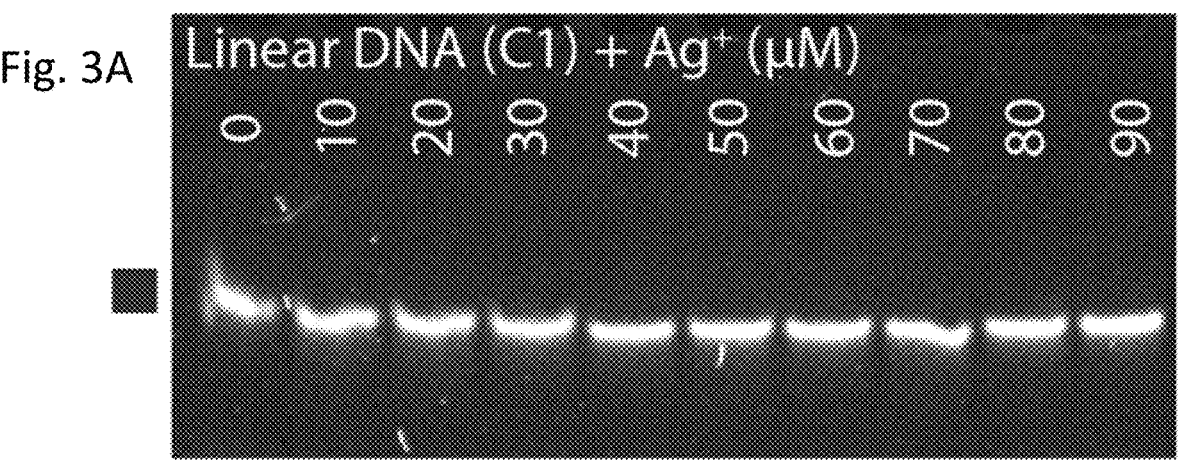
Figure 3B:
Figure 3C:
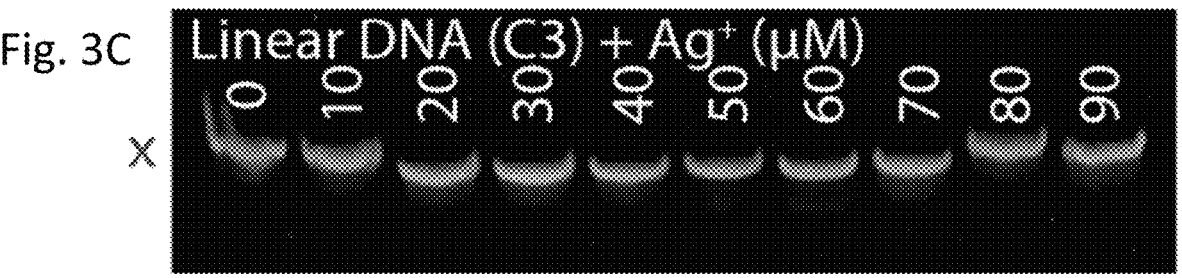
Figure 3D:
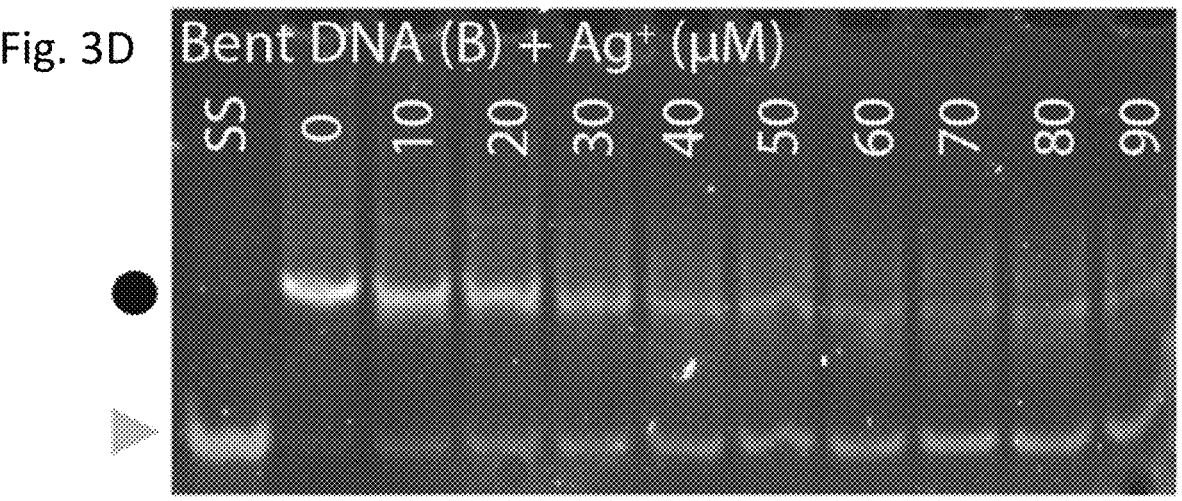

Here, we demonstrate that the disclosed method sensitively measures the interactions between DNA and Ag$^+$ ions. First, we examined the effect of Ag$^+$ ions (0-90 µM) on linear double-stranded DNA (construct C1) and observed no changes with gel electrophoresis (FIG. 2A, and squares in FIG. 2E). In addition, similar to the experiments with Mg$^{2+}$ ions, two other controls with both double-stranded segments and single-stranded overhangs (constructs C2 and C3) were tested (FIGS. 3B and 3C). Again, little changes were observed (▲ triangles and × in FIG. 3E). In contrast, using the bent DNA amplifiers, the interactions between DNA and Ag$^+$ ions were easily observed at 10 µM of Ag$^+$ ions, as shown in FIG. 3D. We note that our method can detect changes at [Ag$^+$]=10 µM, while, without amplification, no such changes were observed with even [Ag$^+$]=90 µM. The "amplification gain" of our method for probing DNA-Ag$^+$ interactions is at least 9.

It was observed that Ag$^+$ ions caused the intensity of the bent DNA band to decrease (circles in FIG. 3D and FIG. 3E), similar to the apparent effect of Mg$^{2+}$ ions. On the other hand, different from Mg$^{2+}$, DNA dimers and higher-order oligomers did not appear significantly in the presence of Ag$^+$ ions. Instead, the band of the single-stranded DNA showed up in the presence of Ag$^+$ ions (indicated by the ▶ triangle in FIG. 3D), suggesting that the DNA-Ag$^+$ interactions are different from the DNA-Mg$^{2+}$ interactions. In addition, the emergence of the single-stranded DNA band indicates that Ag$^+$ ions likely affect DNA hybridization, which is not surprising as Ag$^+$ ions have been found to interact with DNA bases, especially cytosine, and possibly induce chain-slippage.

Figure 3G:
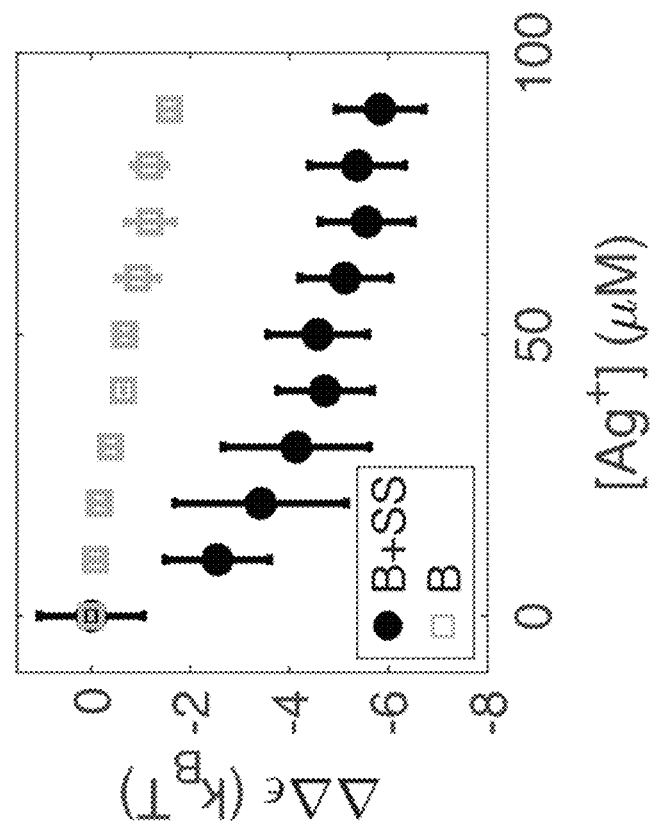
Figure 3F:
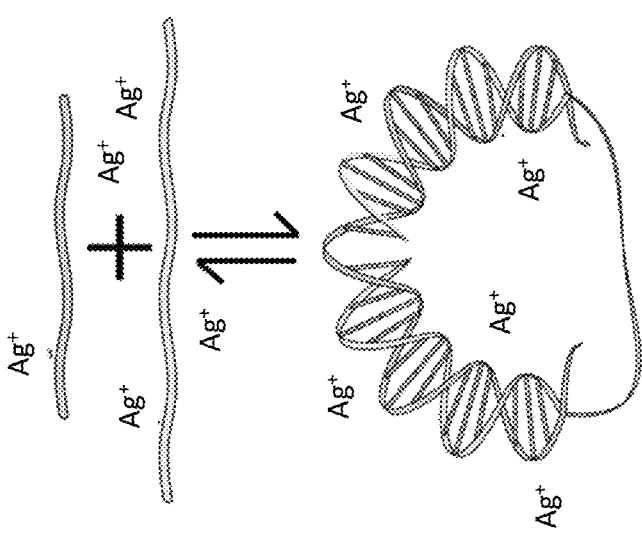

To quantify the DNA-Ag$^+$ interactions, we focused on the hybridization "reaction" of DNA as shown in FIG. 3F. With Eq. (1) and the equilibrium condition $\mu_b = \mu_{ss}$, we have, $$\Delta \epsilon = 2\epsilon_{ss} - \epsilon_b = k_B T \ln\left(\frac{x_b}{x_{ss}^2}\right) \quad (8)$$

and $$\Delta\Delta\epsilon = k_B T \left[\ln\left(\frac{x_b^+}{x_b^-}\right) - 2\ln\left(\frac{x_{ss}^+}{x_{ss}^-}\right)\right] \quad (9)$$

If we normalize the molar fractions to the control (i.e., $[Ag^+]=0$ μM), $\varphi_b^- = x_b^-/x_b^- = 1$, $\varphi_b^+ = x_b^+/x_b^-$, $\varphi_{ss}^- = x_{ss}^-/x_b^-$, and $\varphi_{ss}^+ = x_{ss}^+/x_b^-$, we obtain $$\Delta\Delta\epsilon = k_B T \left[\ln\left(\frac{x_b^+}{x_b^-}\right) - 2\ln\left(\frac{\varphi_{ss}^+}{\varphi_{ss}^-}\right)\right] \quad (10)$$

We estimated $\Delta\Delta\epsilon$ from the experimental data (circles and ▲ triangles in FIG. 3E) and found that $\Delta\Delta\epsilon$ decreased with increasing $[Ag^+]$ as shown in FIG. 3G (black circles).

We note that the dependence of $\Delta\Delta\epsilon \sim k_B \ln(\varphi_b^+)$ (i.e., using the monomer band only) is also able to capture the main feature of $\Delta\Delta\epsilon$ in the presence of $Ag^+$ ions (i.e., $\Delta\Delta\epsilon$ decreases as $[Ag^+]$ increases), as shown in FIG. 3G (squares). However, unlike the result for $Mg^{2+}$ ions, the estimations based on the $\Delta\Delta\epsilon \sim \ln(\varphi_b^+)$ dependence are quantitatively off. The reason for this deviation is that the intensities of the dimer bands stay constant in the presence of $Mg^{2+}$ ions (▶ triangles in FIG. 2D) but the intensities of the single-stranded bands increase steadily in the presence of $Ag^+$ ions (▷ triangles in FIG. 3D).

Example 2: Comparison of DNA-Analyte Interactions

Having demonstrated that interactions between DNA and $Mg^{2+}$ or $Ag^+$ ions, which are not detectable using gel electrophoresis without amplification, can be easily measured using our molecular amplifiers, we sought to test other DNA interactions.

DNA amplifiers were used to measure and quantify the interactions of DNA with 12 additional salts and oligonucleotide interacting compounds. The analytes can be classified into four categories: inorganic molecules (i.e., salts), organic molecules, DNA intercalators, and anticancer drugs, as shown in Table 2.

TABLE 2

Tested molecules using the self-assembled mechanical-energy-based amplifiers.

| Molecule | Category | Concentrations |
|---|---|---|
| $MgCl_2$ | Inorganic | 0, 1, 2, 3, 4, 5, 6, 7 mM |
| $MgSO_4$ | Inorganic | 0, 1, 2, 3, 4, 5, 6, 7 mM |
| KCl | Inorganic | 0, 1, 2, 3, 4, 5, 6, 7 mM |
| $CaCl_2$ | Inorganic | 0, 1, 2, 3, 4, 5, 6, 7 mM |
| $Al(NO_3)_3$ | Inorganic | 0, 16, 32, 48, 64, 80, 96, 112 μM |
| $Zn(NO_3)_2$ | Inorganic | 0, 30, 60, 90, 120, 150, 180, 210 μM |
| $AgNO_3$ | Inorganic | 0, 10, 20, 30, 40, 50, 60, 70, 80, 90 μM |
| Guanidine | Organic | 0, 1, 2, 3, 4, 5, 6, 7 mM |
| Putrescine | Organic | 0, 0.5, 1, 2, 4, 8, 16, 32 mM |
| Spermidine | Organic | 0, 6, 12, 18, 24, 30, 36, 42 μM |
| Thiamine | Organic | 0, 36, 72, 108, 144, 180, 300, 600 μM |
| Ethidium Bromide | Intercalator | 0, 381, 400, 419, 438, 457, 476, 495 μM |
| SYBR Safe | Intercalator | 0, 25, 50, 60, 70, 80, 90, 100 μM |
| Ganciclovir | Anticancer | 0, 1, 2, 3, 4, 5, 6, 7 mM |

The experimental procedure for the gel electrophoresis experiments is the same as described above. The quantification of the bands in gels was done in a similar way, as described above, with one modification. Before performing "gel analysis" in ImageJ, the function "Subtract Background" in ImageJ was applied to remove background. The purpose of this extra step is to reduce human bias when quantifying the band-intensities. On the other hand, we point out that the exact values of the band-intensities after removing background will be different from those without background-subtraction (as did in the methods described above).

Inorganic Salts

Figure 4A:
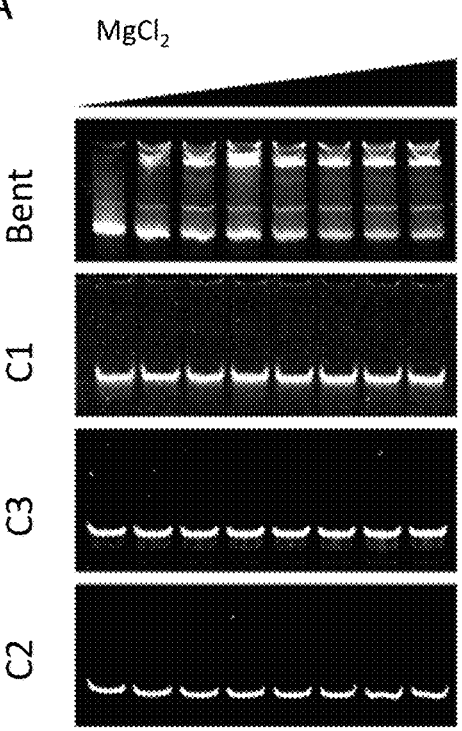
FIGS. 4A-4G illustrate the probing DNA-molecule interactions using bent DNA molecules.
Figure 4B:
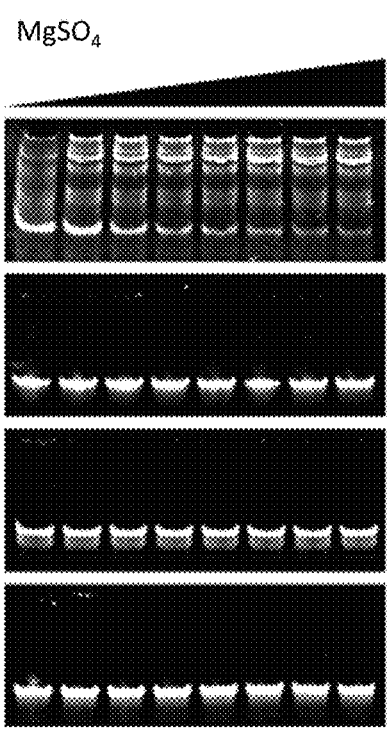
Figure 4E:
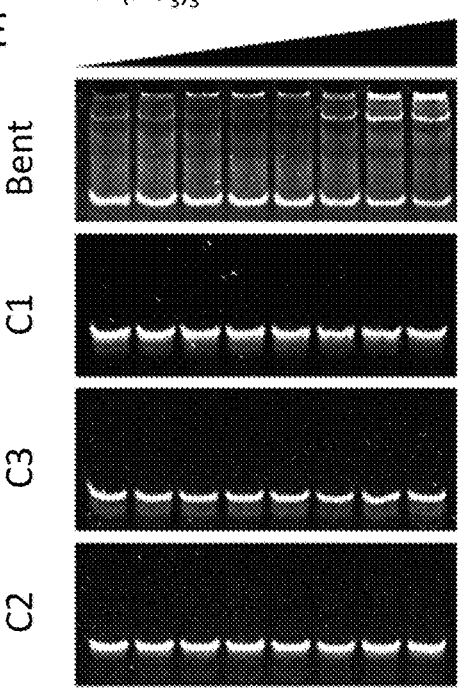
Figure 4F:
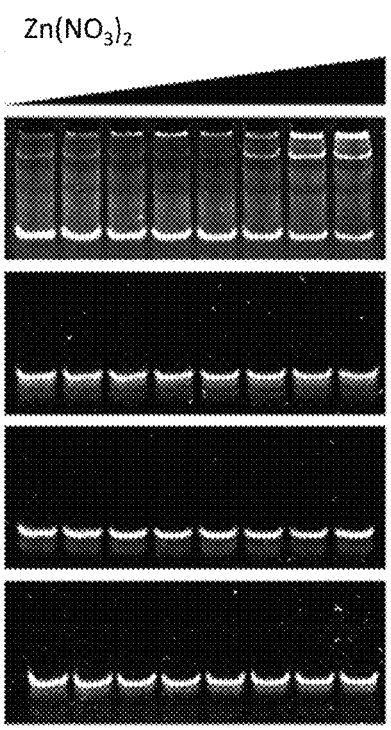
Figure 4C:
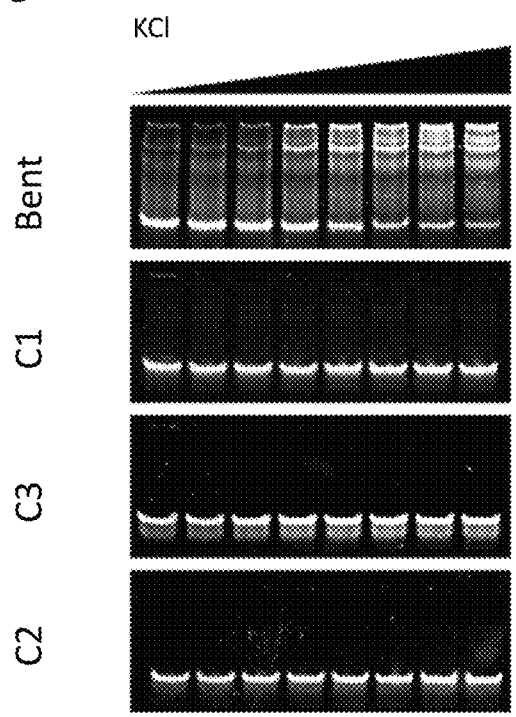
Figure 4D:
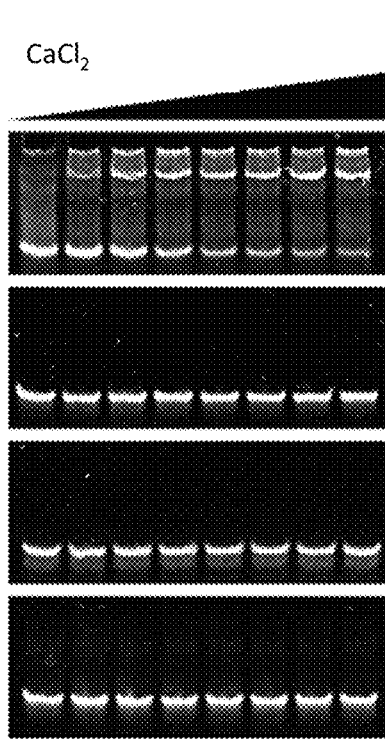
Figure 4G:
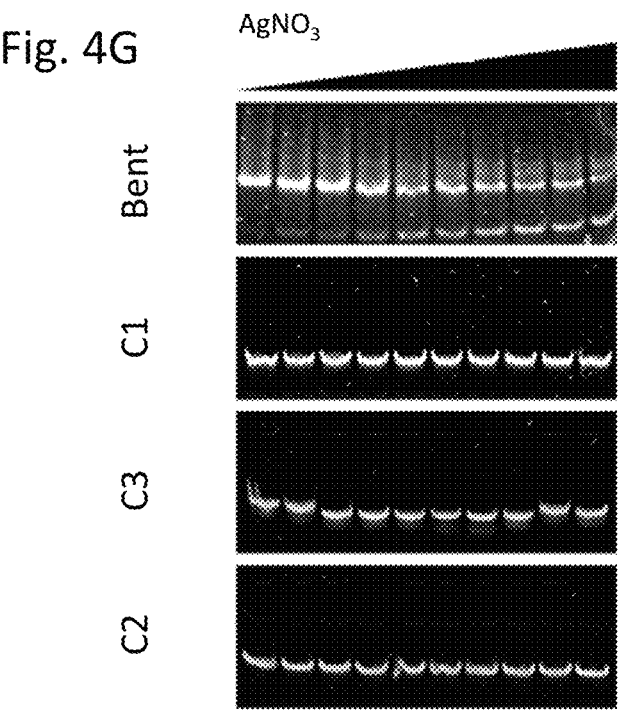
Figure 5A:
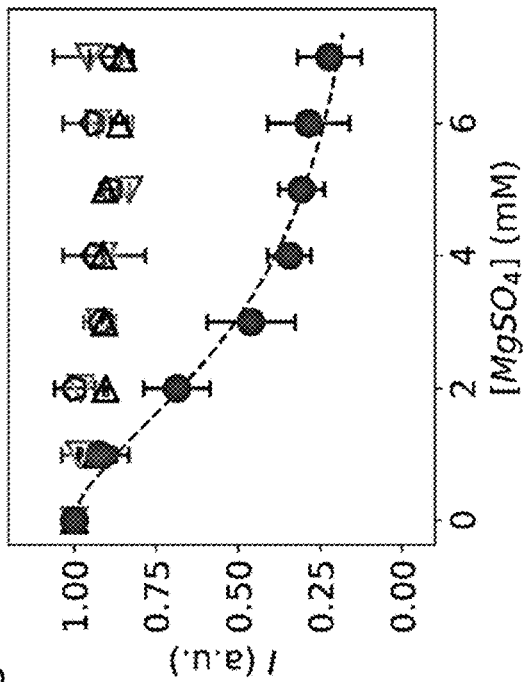
FIGS. 5A-5G illustrate the probing DNA-molecule interactions using bent DNA molecules.
Figure 5B:
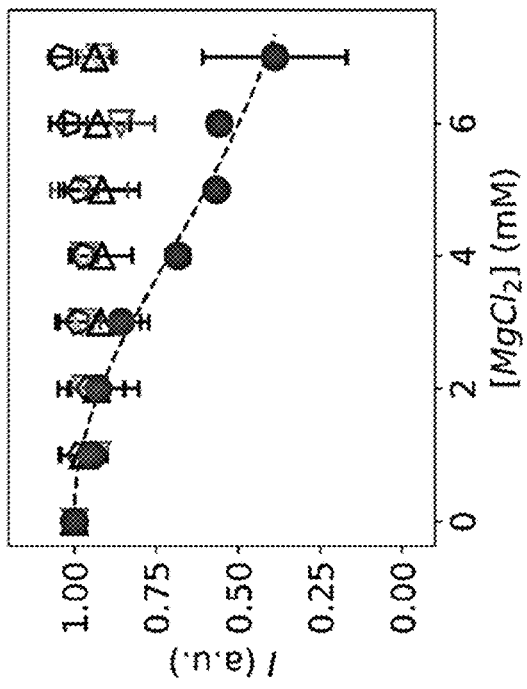
Figure 5E:
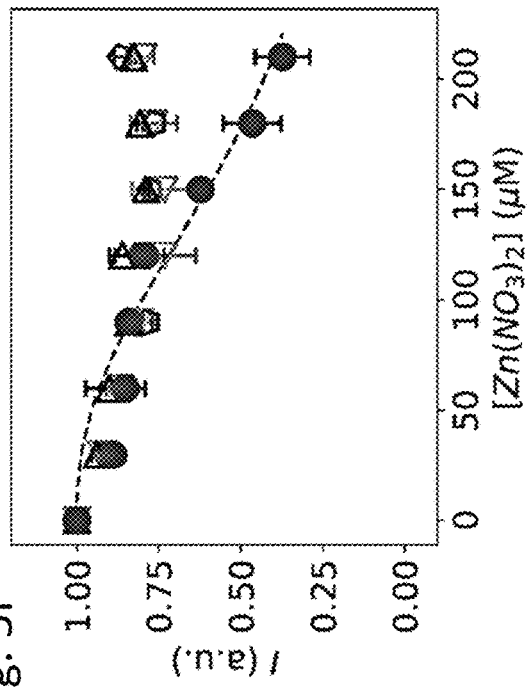
Figure 5F:
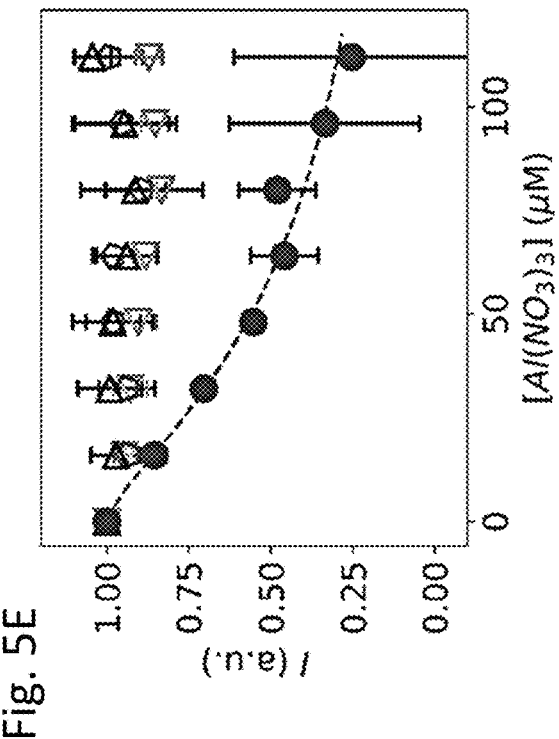
Figure 5D:
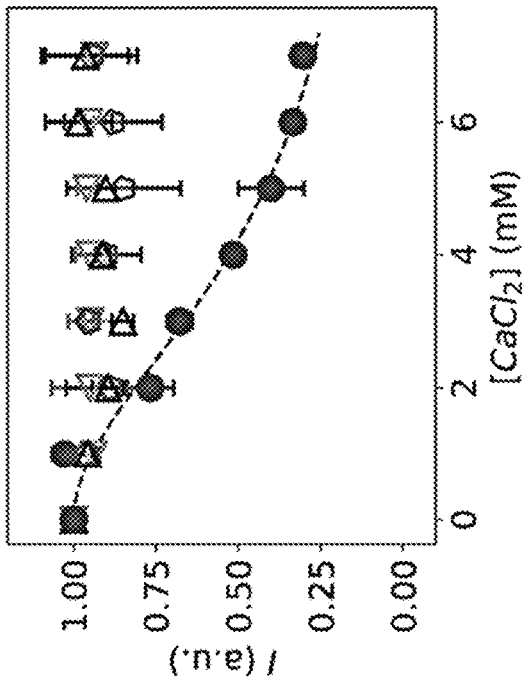
Figure 5C:
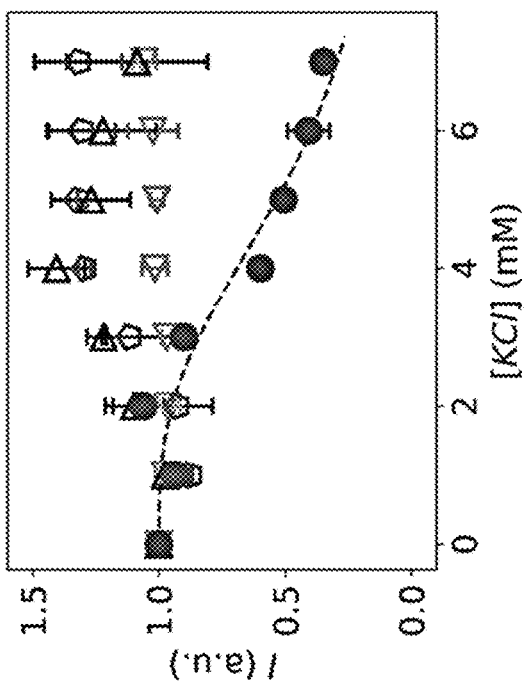
Figure 5G:
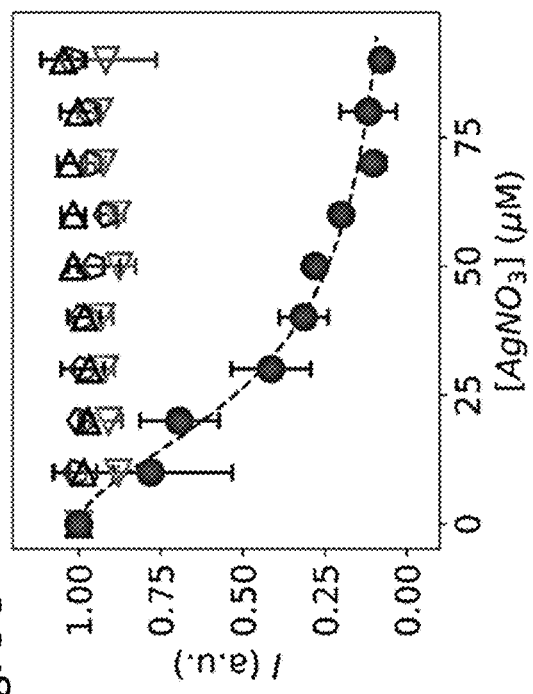

In the absence of amplification (i.e., with normal linear double-stranded DNA), the DNA molecules treated with the tested inorganic salts in the described ranges of concentrations (Table 2) did not show any observable or significant differences in gel electrophoresis (FIGS. 4A-4G, rows indicated by "C1", "C3", and "C2"). In contrast, when amplifying the signal of the DNA interactions with the various molecules using the bent DNA molecules, the effects of the molecules at the same concentrations were observed (FIGS. 4A-4G, rows indicated by "Bent"): the intensities of the bent DNA bands decreased as the concentrations of the molecules increased. In addition, heavier bands corresponding to dimer/trimer/oligomer loops of DNA appeared in the presence of all the tested inorganic salts (FIG. 4A-4F) except $AgNO_3$. A lighter band corresponding to single-stranded DNA showed up when $AgNO_3$ was present (FIG. 4G).

The changes in the intensities of the band of bent DNA molecules were quantified by examining the dependence of the band-intensity of the bent DNA on the concentrations of the tested inorganic salts, as shown in FIGS. 5A-5F. The amplification effects of the bent DNA molecules were observed once again when comparing the dependence of the band-intensity of the linear DNA controls on the same concentrations of the tested inorganic salts (FIGS. 5A-5F).

Figure 6A:
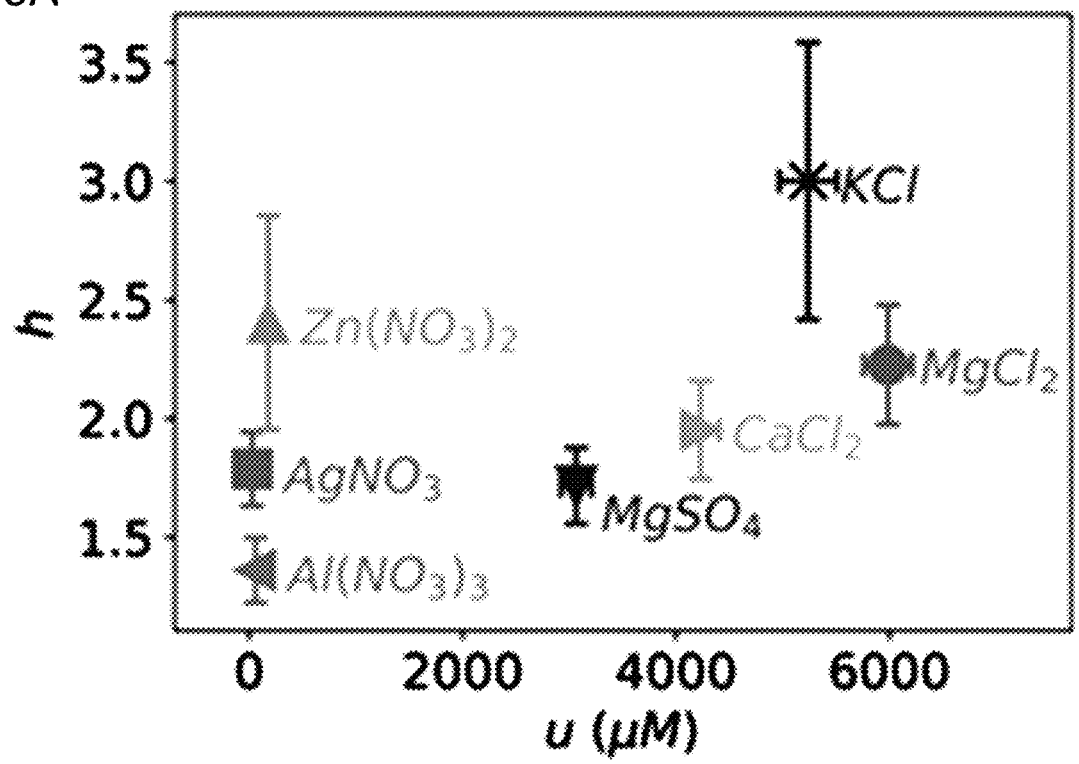
FIGS. 6A-6B illustrate fitted parameters h and u determined with the modified Hill equation for the tested salts.
Figure 6B:
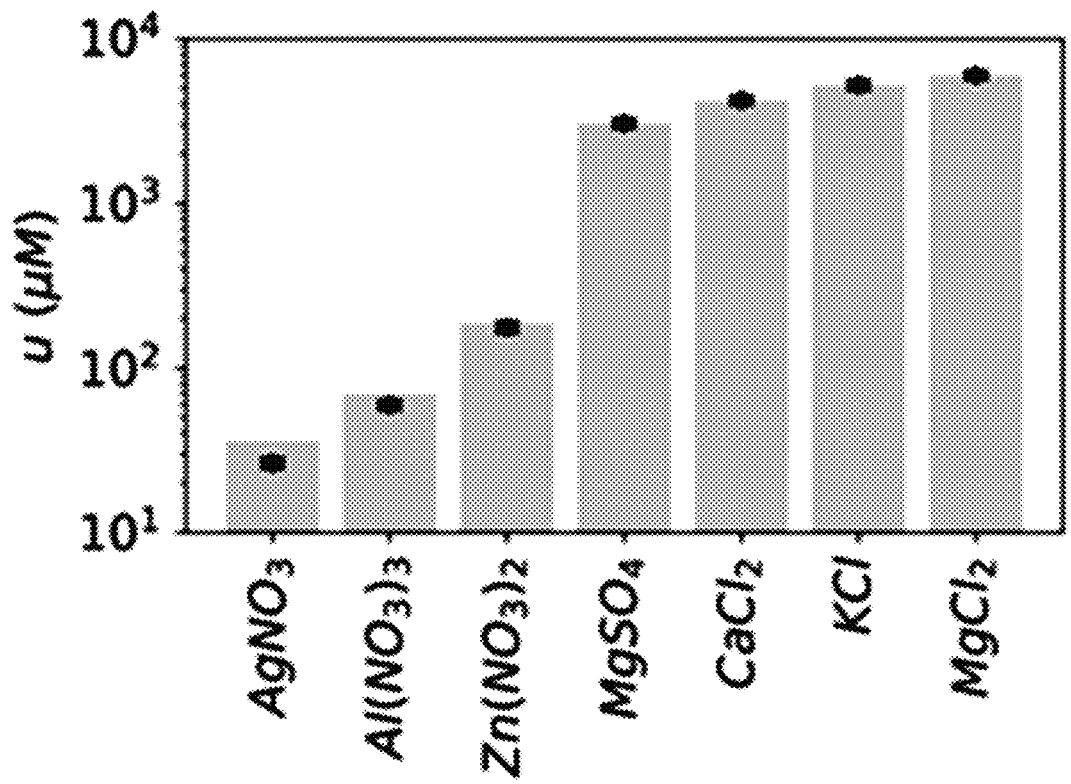

To further quantify the strength of the DNA interactions with these inorganic salts detected by our bent DNA amplifiers, we fitted the normalized intensities of the bands of DNA bows $I_B$ as functions of the concentrations of the salts using an equation derived from the Hill equation that has been extensively used for characterizing the binding between ligands and macromolecules, $$I_B = 1 - \frac{c^h}{c^h + u^h} = \frac{u^h}{c^h + u^h} \quad (11)$$

where c is the concentration of the tested salts, h is the Hill coefficient, and u is the characteristic concentration of the tested salts producing half intensity of the band of DNA bows in the absence of the salts. It turns out that the modified Hill equation fitted all the data very well (FIGS. 5A-5F). The fitted parameters (h and u) were presented in FIG. 6A for the seven tested inorganic salts. In addition, the characteristic concentrations (u) for different salts were compared in FIG. 6B, which suggested that $Al(NO_3)_3$, $Zn(NO_3)_2$ and $AgNO_3$ showed stronger effects on DNA, compared to $MgCl_2$, $MgSO_4$, KCl, and $CaCl_2$. We note that the first three ($Al^{3+}$, $Zn^{2+}$, and $Ag^+$) have been extensively reported to be toxic to bacteria and cells, while the other group ($Mg^{2+}$, $K^+$, $Ca^{2+}$) are essential ions for various cellular processes.

To summarize, the additional tests with several inorganic salts supported our claim that the self-assembled mechanical-energy-based amplifiers are able to amplify the interactions of various inorganic molecules with DNA, make the interactions easily detectable, and quantify the interactions of DNA with various molecules.

Oligonucleotide Interacting Compounds

Figure 7A:
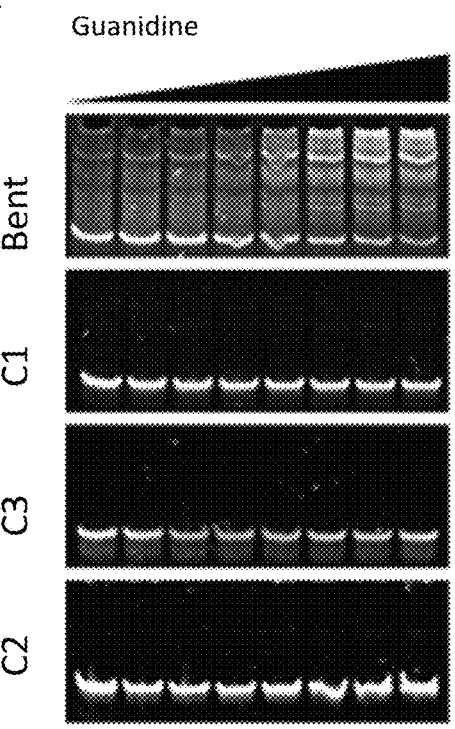
FIGS. 7A-7G illustrate the probing DNA-molecule interactions using bent DNA molecules.
Figure 7B:
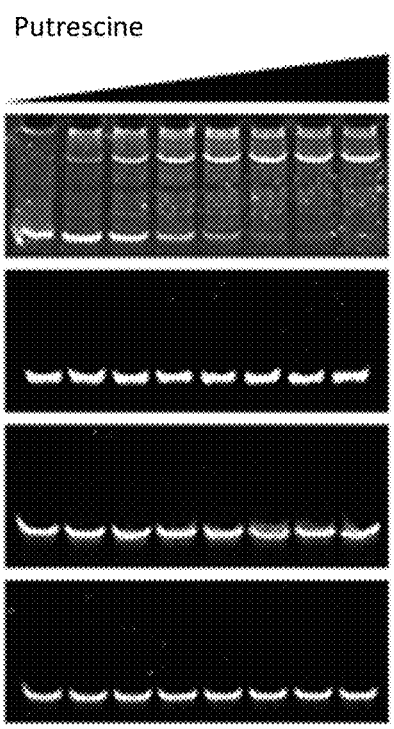
Figure 7E:
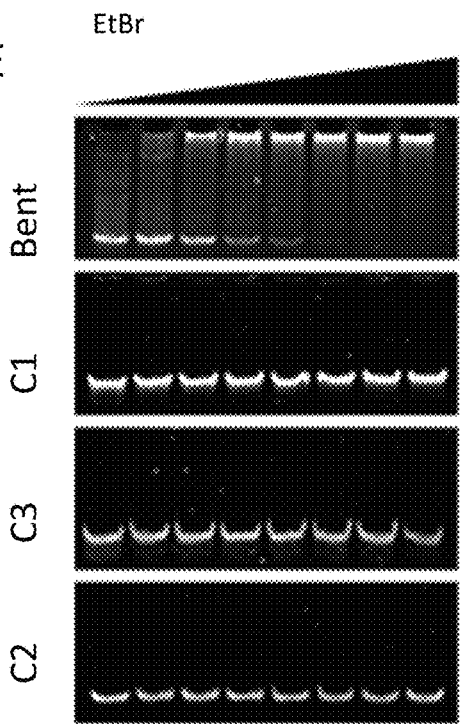
Figure 7F:
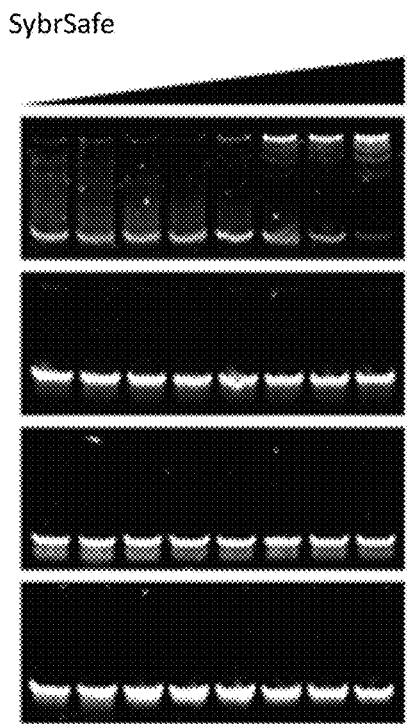
Figure 7C:
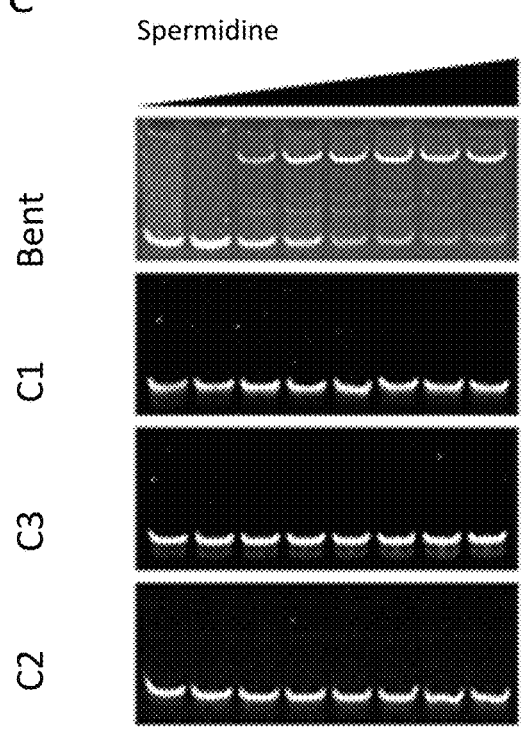
Figure 7D:
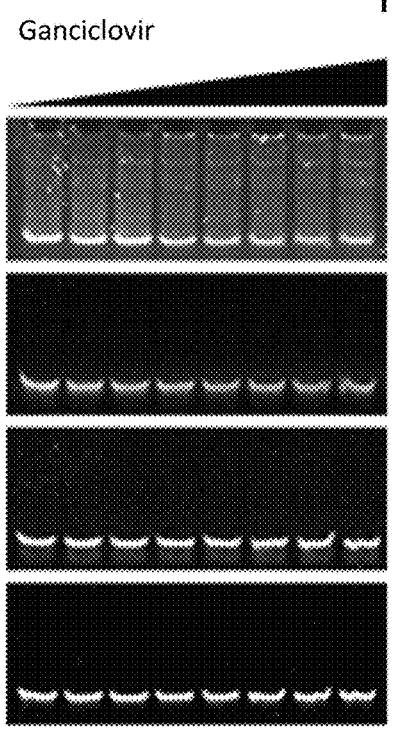
Figure 7G:
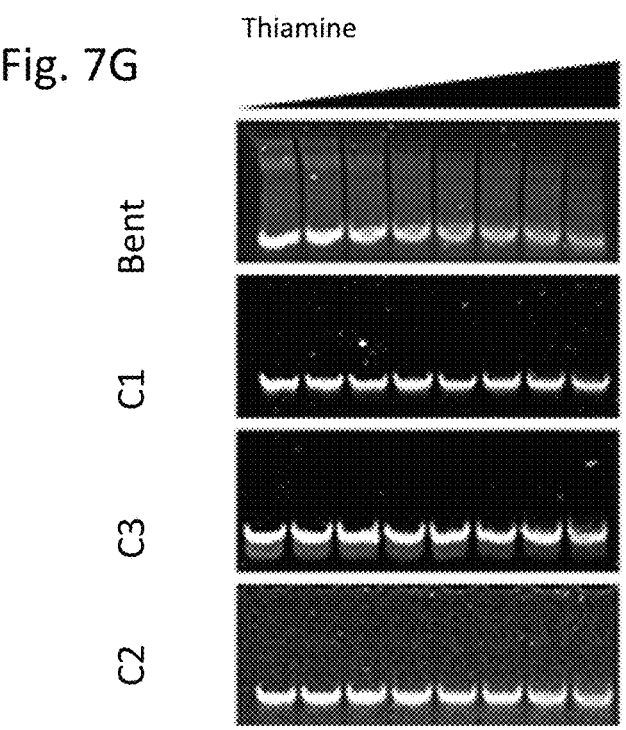
Figure 8B:
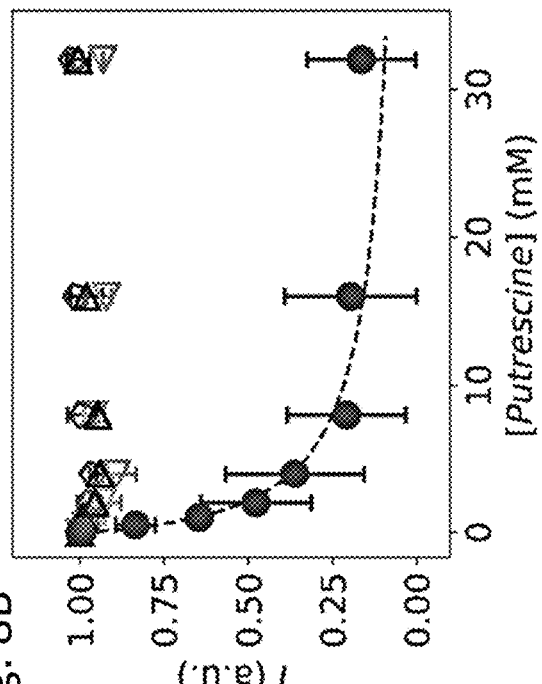
FIGS. 8A-8G illustrate the probing DNA-molecule interactions using bent DNA molecules.
Figure 8F:
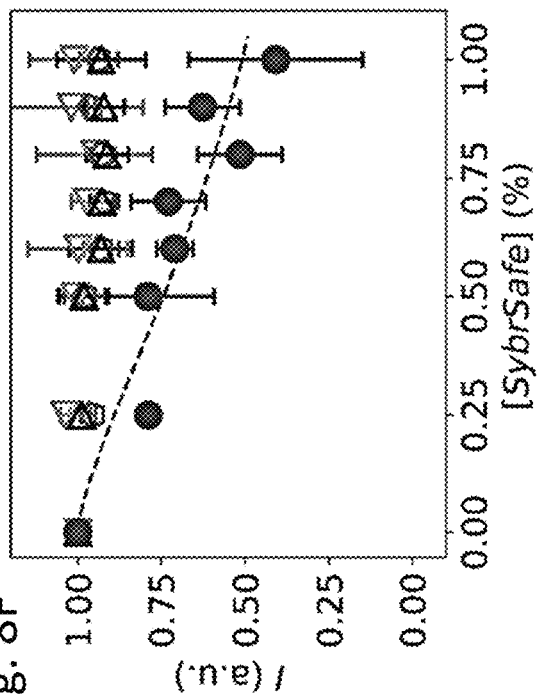
Figure 8A:
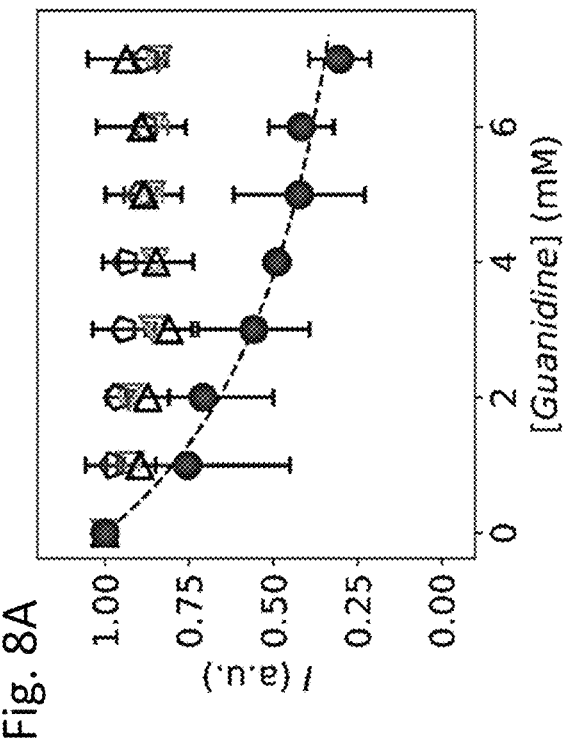
Figure 8E:
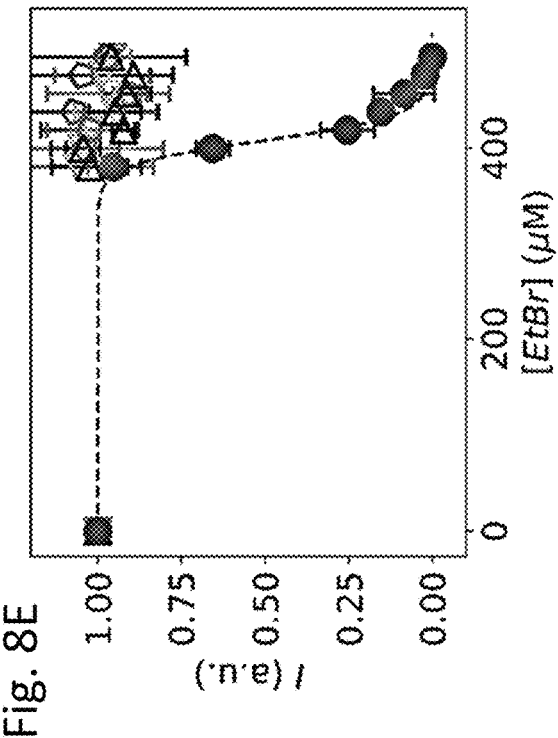
Figure 8D:
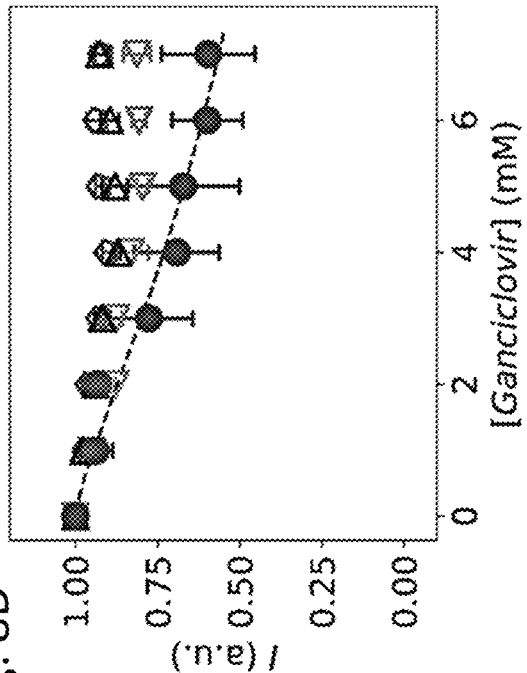
Figure 8C:
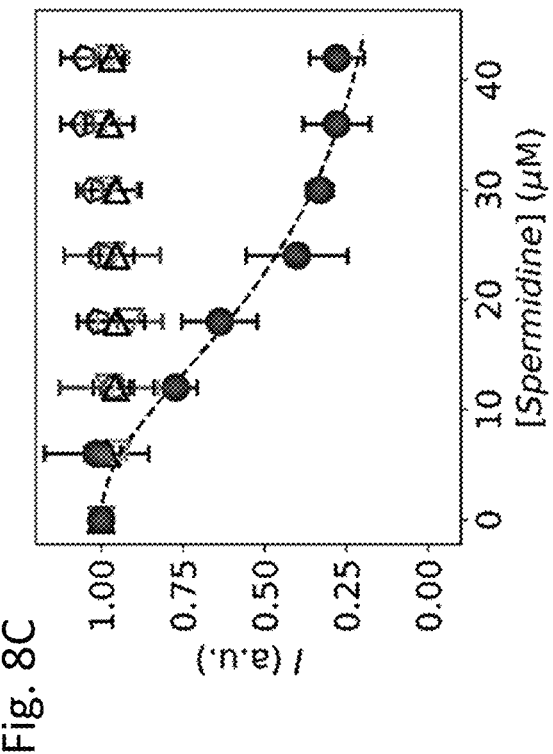
Figure 8G:
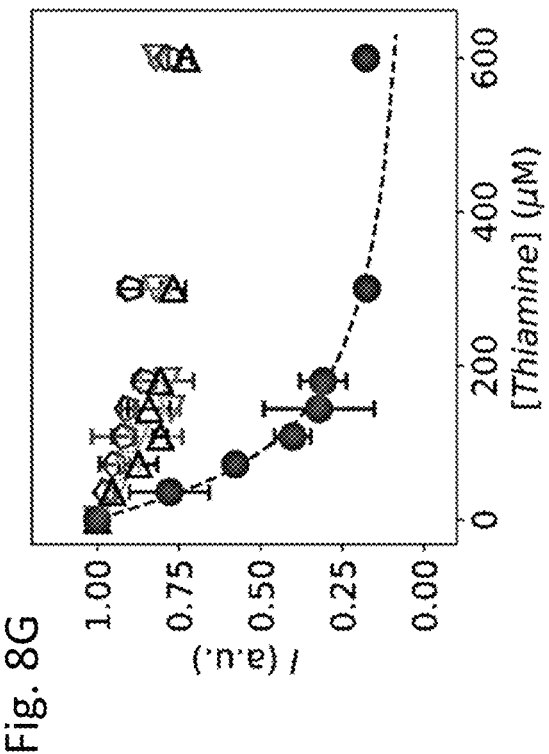

In the absence of amplification (i.e., with normal linear double-stranded DNA), the DNA molecules treated with the tested organic molecules in the described ranges of concentrations (Table 2) did not show any observable or significant differences in gel electrophoresis (FIGS. 7A-7F, rows indicated by "C1", "C3", and "C2"). In contrast, when amplifying the signal of the DNA interactions with the various molecules using the bent DNA molecules, the effects of the molecules at the same concentrations were observed (FIGS. 7A-7F, rows indicated by "Bent"): the intensities of the bent DNA bands decreased as the concentrations of the molecules increased. In addition, heavier bands corresponding to dimer/trimer/oligomer loops of DNA appeared in the presence of all the tested inorganic salts (FIG. 7A-7F) except thiamine, for which the bands became dimmer instead (FIG. 7G).

The changes in the intensities of the band of bent DNA molecules were quantified by examining the dependence of the band-intensity of the bent DNA on the concentrations of the tested organic molecules, as shown in FIGS. 8A-8F. The amplification effects of the bent DNA molecules were observed once again when comparing the dependence of the band-intensity of the linear DNA controls on the same concentrations of the tested organic molecules (FIGS. 8A-8F).

Figure 9A:
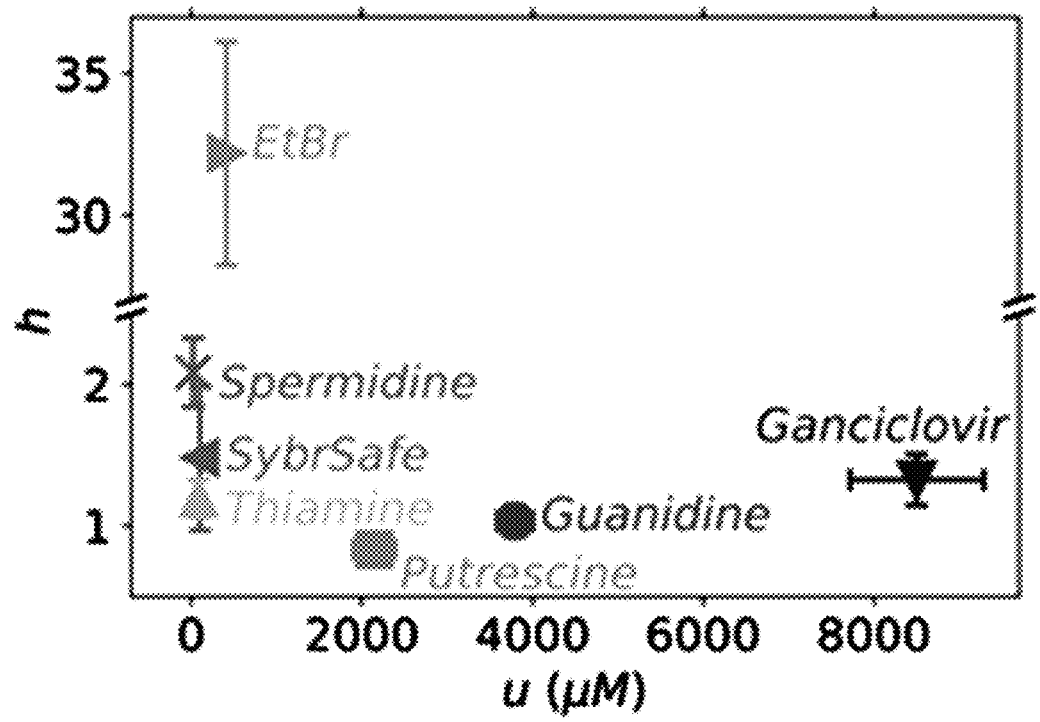
FIGS. 9A-9B illustrate fitted parameters h and u determined with the modified Hill equation for the tested oligonucleotide interacting compounds.
Figure 9B:
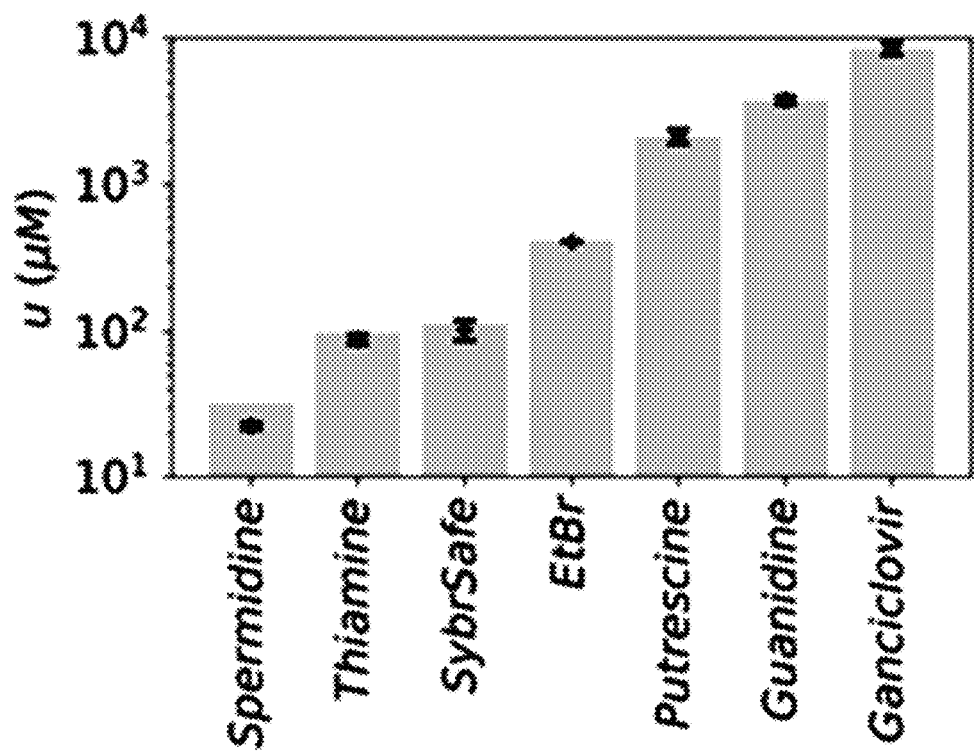

To further quantify the strength of the DNA interactions with these organic molecules detected by our bent DNA amplifiers, we fitted the normalized intensities of the bands of DNA bows $I_B$ as functions of the concentrations of the organic molecules using the modified Hill equation. It was observed that the modified Hill equation fitted all the data very well (FIGS. 8A-8F). The fitted parameters (h and u) were presented in FIG. 9A for the seven tested organic molecules. In addition, the characteristic concentrations (u) for different salts were compared in FIG. 9B.

To summarize, the additional tests with oligonucleotide interacting compounds show that the self-assembled mechanical-energy-based amplifiers are able to amplify the interactions of various organic molecules with DNA, make the interactions easily detectable, and quantify the interactions of DNA with various molecules.

Example 3: Fluorescent Detection of DNA-Analyte Interaction

Fluorescence was used to detect the amplified interactions of DNA with the various salts/molecules.

The DNA strands for fluorescence detection shared the same sequence as those in the gel electrophoresis experiments above. However, the shorter DNA strand for constructing the bent DNA molecule was fluorescently labeled at the two ends using Cy3 (donor) and Cy5 (acceptor) fluorescent dyes. As an example, the full sequence of the shorter strand purchased from IDT-DNA was: /5Cy3/CTG CTG AAT TCT GTG GAG TCG TCG TAT GTC/3Cy5Sp/ (SEQ ID NO: 7), while the sequence of the longer stand remained unlabeled: CAC AGA ATT CAG CAG CAG GCA ATG ACA GTA GAC ATA CGA CGA CTC (SEQ ID NO: 2).

The DNA samples were prepared similarly to those in the gel electrophoresis experiments above. Briefly, the longer and shorter DNA strands were mixed at equal molar amount in background buffer (0.4 mM Tris-HCl with pH adjusted to 7.5 and 0.5 mM NaCl) to reach a final concentration of 2 µM. Solutions of $MgCl_2$ were added to the DNA samples to reach concentrations of $Mg^{2+}$ ions at 0 µM (control), 0.3 µM, 0.75 µM, 1.5 µM, 3 µM, 6.25 µM, 12.5 µM, 25 µM, 50 µM, 100 µM, and 200 µM. The mixtures were heated to 75° C. for 2 minutes, and gradually cooled down to 22° C. (room temperature) in 5 hours. The mixtures were incubated at 22° C. for overnight to allow full equilibrium, followed by fluorescence measurements on the second day.

Figure 10A:
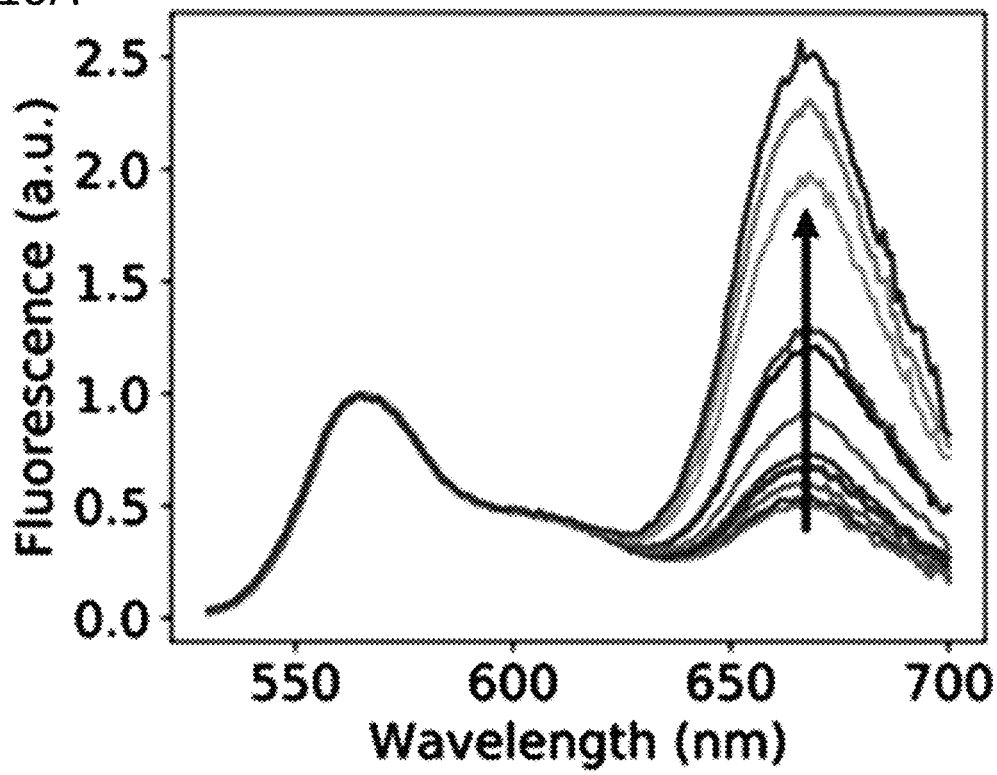
FIGS. 10A-10B illustrate the detection of a spectroscopic feature that depends on the analyte's concentration.

The fluorescence measurements were performed on a Synergy H1 Hybrid Multi-Mode Reader from BioTek. Briefly, the prepared DNA samples were diluted by a fold of three in the background buffer, and 50 µL of the diluted samples were loaded into wells of a 96-well plate (Cornings). The fluorescence emission spectrum were measured with an excitation wavelength at 500 nm and emission wavelengths ranging from 530 nm to 700 nm (step-size=1 nm for the wavelength scanning). The spectral data were first rescaled so that the emission peak of the donor (Cy3, ~566 nm) became one (FIG. 10A). The rationale of the rescaling operation is that any changes in the fluorescence resonance energy transfer (FRET) efficiency between the donor (Cy3) and acceptor (Cy5) due to possible conformational changes of the bent DNA molecules could be directly read out from the emission peak of the acceptor (Cy5, ~667 nm). As shown in FIG. 10A, the emission peak of the acceptor increased at higher concentrations of the $Mg^{2+}$ ions (indicated by the black arrow).

Figure 10B:
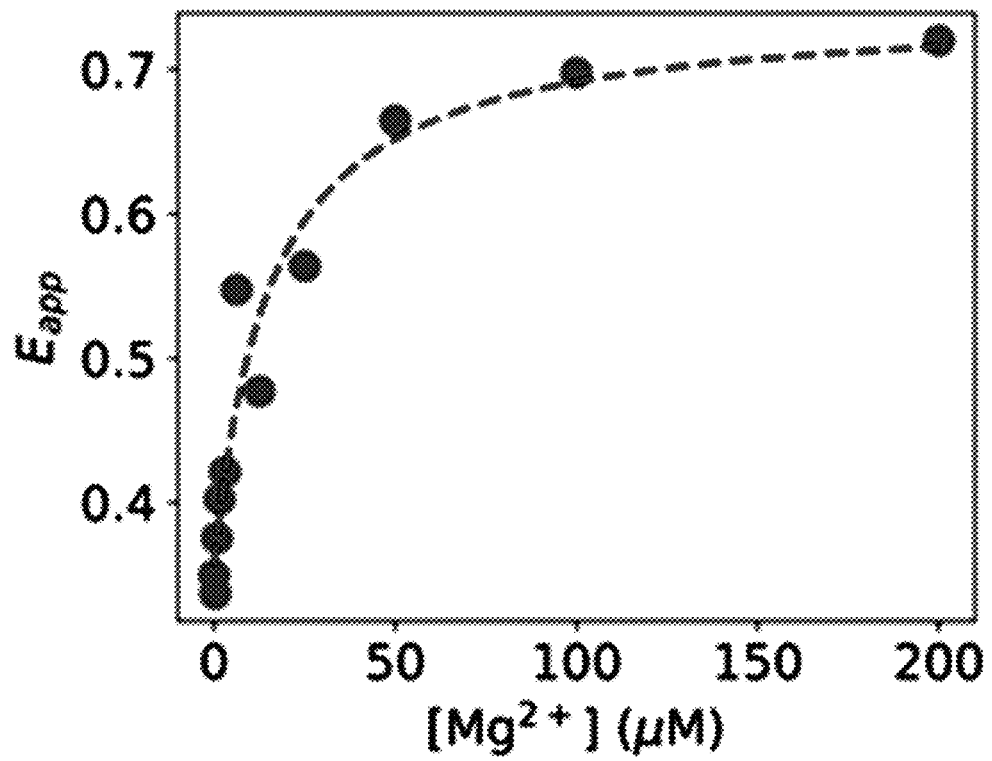

More quantitatively, we estimated the apparent FRET efficiency from the spectral data, $$E_{app} = \frac{I_A}{I_D + I_A} \tag{12}$$

where $I_D$ is the fluorescence of the donor, and $I_A$ is the fluorescence of the acceptor. It is noted that the current method for estimating the FRET efficiency was chosen for simplicity; however, more sophisticated or accurate ways can be used for calculating $E_{app}$. The dependence of the apparent FRET efficiencies of the bent DNA molecules on the concentration of $Mg^{2+}$ is shown in FIG. 10B, which is similar to the Michaelis-Menten (MM) kinetics. Fitting the data using the MM kinetics showed that the Michaelis constant $K_M=(15\pm6)$ µM.

I claim:

1. A method for detecting the interaction of an analyte and a mechanically-strained oligonucleotide construct, the method comprising:
   providing a solution, the solution comprising the mechanically-strained oligonucleotide construct and the analyte;
   detecting at least one detectable characteristic of the mechanically-strained oligonucleotide;
   wherein the mechanically-strained oligonucleotide construct comprises a first oligonucleotide, the first oligonucleotide comprising a first domain and a second domain in order from 5' to 3', and a second oligonucleotide, the second oligonucleotide comprising a first complementary domain, a single-stranded domain, and a second complementary domain in order from 5' to 3';
   wherein the first domain and the first complementary domain are completely or partially complementary and capable of completely or partially hybridizing with each other;
   wherein the second domain and the second complementary domain are completely or partially complementary and capable of completely or partially hybridizing with each other; and
   wherein the at least one detectable characteristic of the mechanically-strained oligonucleotide is (i) a concentration of the mechanically-strained oligonucleotide construct, a component of the mechanically-strained oligonucleotide construct, a higher-order construct, or any combination thereof, and/or (ii) a spectroscopic feature.

2. The method of claim 1, wherein the mechanically-strained oligonucleotide construct comprises $N_d$ complementary base pairs and $N_d$ is greater than or equal to 10 and/or $N_d$ is less than or equal to 100.

3. The method of claim 1, wherein the mechanically-strained oligonucleotide construct comprises $N_s$ unpaired bases and $N_s$ is greater than or equal to 5 and/or $N_s$ is less than or equal to 80.

4. The method of claim 1, wherein the analyte comprises an ion or an oligonucleotide interacting compound.

5. The method of claim 4, wherein the ion is a cation and/or an anion.

6. The method of claim 4, wherein the oligonucleotide interacting compound is an oligonucleotide intercalating compound, an oligonucleotide groove binding compound, or a covalent oligonucleotide binding compound.

7. The method of claim 1, further comprising separating the solution.

8. The method of claim 7, wherein the solution is separated by electrophoresis.

9. The method of claim 1, wherein the mechanically-strained oligonucleotide comprises a chromophore.

10. The method of claim 1, further comprising irradiating the solution.

11. The method of claim 1, wherein the detectable characteristic is indicative of the presence or absence of the interaction of the analyte and the mechanically-strained oligonucleotide.

* * * * *

SEQUENCE LISTING

<160> NUMBER OF SEQ ID NOS: 7

<210> SEQ ID NO 1
<211> LENGTH: 30
<212> TYPE: DNA
<213> ORGANISM: Artificial Sequence
<220> FEATURE:

-continued

<223> OTHER INFORMATION: synthetic

<400> SEQUENCE: 1
ctgctgaatt ctgtggagtc gtcgtatgtc                              30

<210> SEQ ID NO 2
<211> LENGTH: 45
<212> TYPE: DNA
<213> ORGANISM: Artificial Sequence
<220> FEATURE:
<223> OTHER INFORMATION: synthetic

<400> SEQUENCE: 2
cacagaattc agcagcaggc aatgacagta gacatacgac gactc             45

<210> SEQ ID NO 3
<211> LENGTH: 25
<212> TYPE: DNA
<213> ORGANISM: Artificial Sequence
<220> FEATURE:
<223> OTHER INFORMATION: synthetic

<400> SEQUENCE: 3
gagatgtcaa gaattccgtc agcac                                   25

<210> SEQ ID NO 4
<211> LENGTH: 25
<212> TYPE: DNA
<213> ORGANISM: Artificial Sequence
<220> FEATURE:
<223> OTHER INFORMATION: synthetic

<400> SEQUENCE: 4
gtgctgacgg aattcttgac atctc                                   25

<210> SEQ ID NO 5
<211> LENGTH: 30
<212> TYPE: DNA
<213> ORGANISM: Artificial Sequence
<220> FEATURE:
<223> OTHER INFORMATION: synthetic

<400> SEQUENCE: 5
tactgtcatt gcctgctgct gaattctgtg                              30

<210> SEQ ID NO 6
<211> LENGTH: 30
<212> TYPE: DNA
<213> ORGANISM: Artificial Sequence
<220> FEATURE:
<223> OTHER INFORMATION: synthetic

<400> SEQUENCE: 6
gtatgtctac tgtcattgcc tgctgctgaa                              30

<210> SEQ ID NO 7
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: Cy3 fluorescent dye tag
<220> FEATURE:
<221> NAME/KEY: misc_feature

```
<222> LOCATION: (30)..(30)
<223> OTHER INFORMATION: Cy5 fluorescent dye tag

<400> SEQUENCE: 7
ctgctgaatt ctgtggagtc gtcgtatgtc                                           30
```